US007314735B2

(12) United States Patent
Goodson et al.

(10) Patent No.: US 7,314,735 B2
(45) Date of Patent: Jan. 1, 2008

(54) IDENTIFICATION AND CHARACTERIZATION OF REFLECTIN PROTEINS FROM SQUID REFLECTIVE TISSUES

(75) Inventors: Wendy J. Goodson, Madison, WI (US); Margaret McFall-Ngai, Middleton, WI (US); Jennifer Kimbell, Honolulu, HI (US); Joseph Horwitz, Los Angeles, CA (US); Ryan Kramer, Kettering, OH (US); Rajesh R. Naik, Dayton, OH (US)

(73) Assignees: The University of Hawaii, Honolulu, HI (US); The Regents of the University of California, Oakland, CA (US); The Governement of the United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 11/070,723

(22) Filed: Mar. 1, 2005

(65) Prior Publication Data

US 2006/0069240 A1    Mar. 30, 2006

Related U.S. Application Data

(60) Provisional application No. 60/549,733, filed on Mar. 2, 2004.

(51) Int. Cl.
*C12P 21/06* (2006.01)
*C07K 14/00* (2006.01)
*G01N 33/53* (2006.01)

(52) U.S. Cl. .................. 435/69.1; 530/350; 435/7.1
(58) Field of Classification Search .................. None
See application file for complete search history.

(56) References Cited

OTHER PUBLICATIONS

Crooks et al., *Reflectins: the unusual proteins of squid reflective tissues*. Science. Jan. 9, 2004, vol. 303, No. 5655, pp. 235-238.*
Cloney, et al., *Chromatophore Organs, Reflector cells ,Iridocytes and Leucophores in Cephalopods*, Zool. 23:581-592 (1983).
Cooper, et al., *Physiological color change in squid iridophores*, Cell Tissue Res. 259:15-24 (1990).
Crookes, et al., *Reflectins: The Unusual Proteins of Squid Reflective Tissues*, Science, 303:235-238 (2004).
Denton, et al., *Mechanism of Reflexion in SilveryLayers of Fish and Cephalopods*, Biol. Sciences, 178:43-61 (1971).
Johnsen, et al., *Cryptic coloration and mirrored sides as camouflage strategies in near-surface pelagic habitats: Implications for foraging and predator avoidance*, Limnol. Oceanogr. 48:1277-1288 (2003).

Johnsen, Sönke, *Cryptic and conspicuous coloration in the pelagic environment*, The Royal Society, published online, Sep. 5, 2001, pp. 1-14.
Laemmli, U.K., *Cleavage of Structural Proteins during the Assembly of the Head of Bacteriophage T4*, Nature, 227:680-685 (1970).
Land, M.F., *The physics and biology of animal reflectors*, Progress in biophysics and molecular biology, 24:75-106 (1972).
Montgomery, et al., *Embryonic Development of the Light Organ of the Sepiolid Squid Euprymna scolopes Berry*. Biol. Bull. 184:296-308 (1993).
Montgomery, et al., *The muscle-derived lens of a squid bioluminescent organ is biochemically convergent with the ocular lens*. The Journal of Biological Chemistry, 267:20999-21003 (1992).
Steinberg-Y frach, et al., *Light-driven production of ATP catalysed by $F_0F_1$-ATP synthase in an artificial photosynthetic membrane*, Nature, 392:479-782 (1998).
Vukusic, et al., *Photonic structures in biology*, Nature, 424:852-855 (2003).
Weis, et al., *Enhanced Production of ALDH-Like Protein in the Bacterial Light Organ of the Sepiolid Squid Euprymna scolopes*. Biol. Bull. 184:309-321 (1993).
Wise, et al., *Optimization of bacteriorhodopsin for bioelectronic devices*, Trends in Biotechnology, 20:387-394 (2002).
Zhang, et al., *Design of nanostructured biological materials through self-assembly of peptides and proteins*, Current Opinion in Chemical Biology, 6:865-871 (2002).
Accession No. AY294649, Jan. 12, 2004.
Accession No. AY294650, Jan. 12, 2004.
Accession No. AY294651, Jan. 12, 2004.
Accession No. AY294652, Jan. 12, 2004.
Accession No. AY294653, Jan. 12, 2004.
Accession No. AY294654, Jan. 12, 2004.
Weiss et al. NCBI Accession No. CAC86921, Mar. 21, 2005.

* cited by examiner

*Primary Examiner*—Robert Mondesi
(74) *Attorney, Agent, or Firm*—Sonnenschein Nath and Rosenthal, LLP

(57) ABSTRACT

A family of reflectin proteins is identified herein that is deposited in flat, structural platelets in reflective tissues of the squid *Euprymna scolopes*. These proteins are encoded by at least six genes in three subfamilies and have no reported homologues outside of squids. Reflectins possess 5 repeating domains, that are remarkably conserved among members of the family. The proteins have a highly unusual composition with four relatively rare residues (tyrosine, methionine, arginine, and tryptophan) comprising ~57% of a reflectin, and several common residues (alanine, isoleucine, leucine, and lysine) occurring in none of the family members. These protein-based reflectors in squids provide a striking example of nanofabrication in animal systems.

9 Claims, 13 Drawing Sheets

A
```
1a  MNRFMNRYRPMFNNMYSNMYRGRYRGMMEPMSRMTMDFQGRYMDSQGRMVDPRYYDYYGRF
1b  MNRFMNKYRPMFNNMYSNMYRGRNRGMMEPMSRMTMDFQGRYMDSQGRMVDPRYYDYYGRF
2a  MNRYMTRFR----NFYGNMYRGRYRGMMEPMSRMTMDFQGRYMDSQGRMVDPRYYDYYGRY
2b  MNRYMNRFR----NFYGNMYRGRYRGMMEPMSRMTMDFQGRYMDSQGRMVDPRFYDYYGRY
2c  MNRYMNRFR----NFYGNMYRGRYRGMMEPMSRMTMDFQGRYMDSQGRMVDPRYYDYYGRY
3a  MNRYMNRFR----NFYGNMCRNRNRGMMEPMSRMTMDFQGRYMDSQGRMVDPRYYDYYGRY
Lf  MNRSMNRYQP--SNMWGNMNRDRYSGMMEPMSRMSMDFQGRHMDSMDRMVDP------GRW
    ***  *.:::    *;:.** * *  ********:***** :*** . *****      **:

1a  NDYDRYYGRSMFNYGWMMDGDRYNRYNRWMDYPERYMDMSGYQMDMSGRWMDMQGRHCNPY
1b  NDYDRYYGRSMFNYGWMMDGDRYNRYNRWMDYPERYMDMSGYQMDMSGRWMDMQGRHCNPY
2a  NDYDRYYGRSMFNYGWMMDGDRYNRYNRWMDYPERYMDMSGYQMDMYGRWMDMQGRHCNPY
2b  NDYDRYYGRSMFNYGWMMDGDRYNRCNRWMDYPERYMDMSGYQMDMYGRWMDMQGRHCNPY
2c  NDYDRYYGRSMFNYGWMMDGDRYNRYNRMDFPERYMDMSGYQMDMYGRWMDMQGRHCNPY
3a  NDYDRYYGRSMFNYGWMMDGDRYNRYNRWMDYPERYMDMSGYQMDMYGRWMDMQGRHCNPY
Lf  NDYDRYYGRSTFNYGWMENGDRFNRNLRPMDFPERYMDMSDYQMDMGGRWMDPYGRQCNPF
    **********  ****** *+**+:*   * **:**********  *****  **:***:

1a  SQWMMYNYNRHGYYPNYSYGRHMFYPERWMDMSNYSMDMYGRYMDRWGRYCNPFSQYMNYY
1b  SQWG-YNYNRHGYYPNYSYGRHMFYPERWMDMSGYQMDMQGRYMDRWGRYCNPFSQYMNYY
2a  SQWMMYNYNRHGYYPNYSYGRHMFYPERWMDMSNYSMDMYGRYMDRWGRYCNPFYQFYNHW
2b  SQWMMYNYNRHGYYPNYSYGRHMFYPERWMDMSNYSMDMYGRYMDRWGRYCNPFYQFYNHW
2c  SQWMMYNYNRHGYYPNYSYGRHMFYPERWMDMSNYSMDMYGRYMDRWGRYCNPFYQFYNHW
3a  SQWMMYNYNRHGYYPNYSYGRHMFYPERWMDMSNYSMDMYGRYMDRWGRYCNPFYHYYNHW
Lf  NQCG---YNRHGYYPGYSYGRNMCYPERWMDMSNYSMDMQGRYMDRRGRHCNPFSQHTNWY
    .  *   ** *+*+.+*  *+**+*:* ** *****:******+***  :*+. *:   *

1a  GRYWNYPGYNNYYYSRNMYYPERYFDMSNWQMDMQGRWMDNQGRYCSPYWNNWYGRHMYYP
1b  GRYWNYPGYNSYYNSRNMFYPERYFDMSNWQMDMQGRWMDNQGRYCSPYWNNWYGRQMYYP
2a  NRYGNYPGYYNYYY---MYYPERYFDMSNWQMDMQGRWMDMQGRYCSPYWYNWYGRHMYYP
2b  NRYGNYPGYYNYYY---MYYPERYFGMSNWQMDMQGRWMDMQGRYCSPYWYNWYGRHMYYP
2c  NRYGNYPGYYNYYY---MYYPERYFDMSNWQMDMQGRWMDMQGRYCSPYWYNWYGRQMYYP
3a  NRSGNNPGYYSYYY---MYYPERYFDMSNWQMDMQGRWMDMQGRYCSPYWYNWYGRQMYYP
Lf  GRYRNYPGDNNYYN-RNMYYPERHFDMSNWQMDMQGRWMDNQGRYNNPYWY---GRNMYQP
    .*  +* **    .**  *;+***:+.+****+****** *** .******     .+:** +

1a  YQNNYFYGRYDYPGMDYSNYQMDMQGRYMDQYG--MN----DYYY------
1b  YQNNYFYGRYDYPGMDYSNYQMDMQGRYMDQYG--MN----DYCY------
2a  YQNYYWYGRYDYPGMDYSNWQMDMQGRWMDMQGRYMD---YPNYYNWY--
2b  YQNYYWYGRYDYPGMDYSNWQMDMQGRWMDMQGRYMD---YPNYYNWNH-
2c  YQNYYWYGRYDYPGMDYSNYQMDMQGRYMDMQGRYMD---YPNYYNWNH-
3a  YQNYYWYGRWDYPGMDYSNWQMDMQGRWMDMQGRYMDPWWMNDSYYNNYYN
Lf  YQNNQWSGRWDYPGMDCG---MDMQGGYMNSN--------EGDYL-----
```

B

| | 1a | 1b | 2a | 2b | 2c | Lf |
|---|---|---|---|---|---|---|
| 1a | -- | | | | | 72.2 |
| 1b | 95.8 | -- | | | | 71.4 |
| 2a | 89.7 | 85.7 | -- | | | 70.5 |
| 2b | 89.0 | 85.0 | 98.2 | -- | | 70.1 |
| 2c | 90.1 | 86.8 | 98.6 | 97.5 | -- | 71.2 |
| 3a | 87.2 | 85.3 | 95.6 | 95.3 | 95.6 | 69.0 |

C

| amino acid | 1a # | 1a % | 2a # | 2a % | 3a # | 3a % |
|---|---|---|---|---|---|---|
| Y | 59 | 19.8 | 62 | 21.9 | 57 | 19.8 |
| M | 42 | 14.6 | 41 | 14.5 | 42 | 14.6 |
| R | 33 | 11.8 | 33 | 11.7 | 34 | 11.8 |
| N | 28 | 9.7 | 23 | 8.1 | 28 | 9.7 |
| G | 24 | 8.3 | 25 | 8.8 | 24 | 8.3 |
| D | 23 | 8.3 | 23 | 8.1 | 24 | 8.3 |
| W | 11 | 5.9 | 15 | 5.3 | 17 | 5.9 |
| S | 15 | 4.9 | 11 | 3.9 | 14 | 4.9 |
| P | 13 | 4.5 | 13 | 4.6 | 13 | 4.5 |
| Q | 13 | 4.5 | 13 | 4.6 | 13 | 4.5 |
| F | 9 | 2.8 | 9 | 3.2 | 8 | 2.8 |
| E | 4 | 1.4 | 4 | 1.4 | 4 | 1.4 |
| H | 4 | 1.4 | 5 | 1.8 | 4 | 1.4 |
| C | 3 | 1.4 | 3 | 1.1 | 4 | 1.4 |
| T | 1 | 0.3 | 2 | 0.7 | 1 | 0.3 |
| V | 1 | 0.3 | 1 | 0.4 | 1 | 0.3 |
| A | 0 | 0 | 0 | 0 | 0 | 0 |
| I | 0 | 0 | 0 | 0 | 0 | 0 |
| L | 0 | 0 | 0 | 0 | 0 | 0 |
| K | 0 | 0 | 0 | 0 | 0 | 0 |

```
1a    ATGAACCGTTTTATGAACAGATACCGACCCATGTTCAACAACATGTATAGCAACATGTACCGCGG
2a            ATGAACCGTTACATGACCCGATTCCGTAACTTCTACGGCAACATGTACCGCGG
3a            ATGAACCGTTACATGAACCGATTCCGTAACTTTTACGGCAACATGTGCCGCAA
Lf                                                            ATGAACAGAGA
                                                              ***  *  *

1a    TAGATACCGAGGTATGATGGAACCCATGTCCCGTATGACCATGGACTTCCAAGGAAGATACATGG
2a    TAGATACCGAGGAATGATGGAACCCATGTCCCGTATGACCATGGACTTCCAAGGAAGATACATGG
3a    CAGAAACCGCGGTATGATGGAGCCGATGTCCCGTATGACCATGGACTTCCAAGGAAGATACATGG
Lf    TAGATACAGTGGTATGATGGAACCCATGTCCAGAATGAGCATGGACTTCCAAGGAAGACACATGG
      ***  ** * ** ******** ** ****** *   **** *********** ***** ******

1a    ACTCCCAAGGAAGAATGGTCGACCCCAGATACTACGACTACTATGGAAGATTCAACGACTATGAC
2a    ACTCCCAGGGAAGAATGGTCGACCCCAGATACTACGACTACTATGGAAGATACAACGACTATGAC
3a    ACTCCCAGGGAAGAATGGTCGACCCCAGGTACTACGACTACTATGGAAGATACAACGACTACGAC
Lf    ACTCCATGGACAGAATGGTCGACCCC----------------GGAAGATGGAACGACTATGAC
      ****   *    *************                  ******  ******** ***

1a    CGTTACTACGGAAGATCCATGTTCAACTACGGCTGGATGATGGACGGTGATAGGTACAACAGATA
2a    CGTTACTACGGAAGATCCATGTTCAACTACGGTTGGATGATGGACGGTGATAGGTACAACAGATA
3a    CGTTATTACGGAAGATCCATGTTCAATTACGGCTGGATGATGGACGGTGATAGGTACAACAGATA
Lf    CGTTACTACGGAAGGTCCACGTTTAATTATGGCTGGATGGAGAACGGTGACAGATTCAACAGGAA
      ***** ******** **** ***  ** ** ** ******   * ******* **  **** **

1a    CAACCGATGGATGGACTACCCCGAGAGGTACATGGACATGTCTGGCTACCAGATGGACATGTCTG
2a    CAACCGATGGATGGACTTCCCCGAGAGGTACATGGACATGTCTGGCTACCAGATGGACATGTACG
3a    CAACCGATGGATGGACTACCCAGAGAGGTACATGGACATGTCTGGCTACCAGATGGACATGTACG
Lf    CCTCCGCCCTATGGACTTCCCCGAGAGGTACATGGACATGTCTGGCTACCAGATGGACATGTACG
       *  ***    ******* *** *************************************** *

1a    GACGCTGGATGGACATGCAGGGACGCCACTGCAACCCGTATAGCCAATGGATGATGTACAACTAC
2a    GACGCTGGATGGACATGCAGGGACGCCACTGCAACCCGTATAGCCAATGGATGATGTACAACTAC
3a    GACGCTGGATGGACATGCAGGGACGCCACTGCAACCCGTACAGCCAATGGATGATGTACAACTAC
Lf    GACGCTGGATGGACCCATACGGACGCCAGTGCAACCCATTCAACCAGTG---------TGGTTAC
      **************   * ********  *******   *  *** **             ***

1a    AACAGACACGGTTACTATCCCAACTACTCCTACGGCCGCCATATGTTCTACCCGGAGAGATGGAT
2a    AACAGACACGGTTACTATCCCAACTACTCCTACGGCCGCCATATGTTCTACCCGGAGAGATGGAT
3a    AACAGACACGGTTACTATCCCAACTACTCCTACGGCCGTCATATGTTCTACCCGGAGAGATGGAT
Lf    AACAGACATGGTTACTATCCTGGCTACTCCTACGGTCGTAACATGTGTTACCCCGAGAGATGGAT
      ********  **********    ************ **  *   *****  * ** *********

1a    GGACATGTCTAACTACTCCATGGACATGTACGGACGTTACATGGACAGGTGGGGACGTTACTGCA
2a    GGACATGTCTAACTACTCCATGGACATGTACGGACGTTACATGGACAGGTGGGGACGTTACTGCA
3a    GGACATGTCTAACTACTCCATGGACATGTACGGACGTTACATGGACAGGTGGGGACGTTACTGCA
Lf    GGACATGTCTAACTACTCCATGGATATGCAGGGACGCTACATGGACAGACGGGGTCGTCATTGCA
      ***********************  *** * ****** ***********    ****  * ****

1a    ACCCGTTCTCCCAGTACATGAATTACTATGGCAGATACTGGAACTACCCCGGGTACAACAACTAT
2a    ACCCGTTCTACCAATTCTACAACCACTGGAACCGCTACGGCAACTACCCCGGGTACTATAACTAC
```

```
3a   ACCCGTTCTATCACTATTACAACCACTGGAACCGCTCCGGCAACAACCCCGGGTACTATAGCTAC
Lf   ACCCGTTCTCTCAGCACACGAATTGGTACGGTAGATATCGGAATTATCCCGGTGATAATAACTAC
     *********  **       **    *    * *   * **  * *****   *  * * ***

1a   TATTACAGCAGAAACATGTACTACCCAGAAAGATACTTCGATATGTCTAACTGGCAGATGGATAT
2a   TACTACA---------TGTACTACCCGGAAAGATATTTCGACATGTCTAACTGGCAGATGGATAT
3a   TACTACA---------TGTACTACCCAGAGAGATACTTCGACATGTCTAACTGGCAGATGGATAT
Lf   TACAACAG---AAACATGTACTATCCCGAGAGACATTTTGATATGTCCAACTGGCAGATGGATAT
     ** **  ***       ****** ** ** *** * ** ** ***** *****************

1a   GCAGGGACGCTGGATGGATAACCAAGGACGCTACTGCAGCCCCTATTGGAACAACTGGTATGGCA
2a   GCAGGGACGCTGGATGGATATGCAGGGACGCTACTGCAGCCCCTATTGGTACAACTGGTATGGCA
3a   GCAGGGACGCTGGATGGATATGCAGGGACGCTACTGCAGCCCCTATTGGTACAACTGGTATGGCA
Lf   GCAGGGACGCTGGATGGATAATCAGGGACGCTACAACAACCCCTA---------CTGGTACGAA
     ******************   ** *********  ** ******         ***** ** *

1a   GACATATGTACTACCCGTACCAGAACAATTATTTCTACGGCCGTTATGACTATCCCGGAATGGAC
2a   GACATATGTACTACCCCTACCAGAACTACTATTGGTACGGCCGTTATGACTATCCCGGGATGGAC
3a   GACAGATGTACTACCCCTACCAGAACTACTATTGGTACGGCCGATGGGACTATCCCGGAATGGAC
Lf   GAAACATGTACCAGCCCTACCAGAATAATCAGTGGTCCGGCCGATGGGACTATCCCGGAATGGAC
     **  ****** *  ** ********  *  *    *  * ******  *  ************

1a   TATTCCAACTATCAGATGGACATGCAGGGACGCTATATGGACCAATACGGAATGAACGACTATTA
2a   TATTCCAACTGGCAGATGGATATGCAGGGACGCTGGATGGATATGCAAGGGCGATACATGGATTA
3a   TATTCCAACTGGCAGATGGATATGCAGGGACGCTGGATGGACATGCAGGGACGATACATGGACCC
Lf   TGCGGTA---------TGGACATGCAGGGAGGTTACATGAATA---ATAGTAATGAAGGGGACTA
      *   *           **** ********  * *  *** *   *   *   *  *  *  *

1a   CTATTAA
2a   TCCCTATAATTATTACAACTGGTATTAA
3a   CTGGTGGATGAACGACTCCTACTACAATAACTACTACAATTAA
Lf   CTATAG
```

```
1a    ATGAACCGTTTTATGAACAGATACCGACCCATGTTCAACAACATGTATAG
1b    ATGAACCGTTTTATGAACAAATACCGACCCATGTTCAACAACATGTATAG
2a              ATGAACCGTTACATGACCCGATTCCGTAACTTCTACGG
2b              ATGAACCGTTACATGAACCGATTCCGTAACTTCTATGG
2c              ATGAATCGTTACATGAACCGATTCCGTAACTTCTACGG
2d              ATGAACCGTTACATGAACCGATTCCGTAACTTCTACGG
3a              ATGAACCGTTACATGAACCGATTCCGTAACTTTTACGG
                * * * * *    * * *     *    * * *    * * * * *    *

1a    CAACATGTACCGCGGTAGATACCGAGGTATGATGGAACCCATGTCCCGTA
1b    CAACATGTACCGCGGTAGAAACCGAGGTATGATGGAGCCCATGTCCCGTA
2a    CAACATGTACCGCGGTAGATACCGAGGAATGATGGAACCCATGTCCCGTA
2b    CAACATGTACCGCGGCAGATACCGAGGGATGATGGAGCCCATGTCCCGTA
2c    CAACATGTACCGCGGTAGATACCGAGGGATGATGGAACCCATGTCTCGTA
2d    CAACATGTACCGCGGTAGATACCGAGGAATGATGGAACCCATGTCCCGTA
3a    CAACATGTGCCGCAACAGAAACCGCGGTATGATGGAGCCGATGTCCCGTA
      * * * * * * * *   * * * *       * * *   * * * *   * *   * * * * * * *   * *   * * * * *   * * * *

1a    TGACCATGGACTTCCAAGGAAGATACATGGACTCCCAAGGAAGAATGGTC
1b    TGACCATGGACTTCCAAGGAAGATACATGGACTCCCAGGGAAGAATGGTC
2a    TGACCATGGACTTCCAAGGAAGATACATGGACTCCCAGGGAAGAATGGTC
2b    TGACCATGGACTTCCAAGGAAGATACATGGACTCTCAGGGAAGAATGGTT
2c    TGACCATGGACTTCCAAGGAAGATACATGGACTCTCAGGGAAGAATGGTC
2d    TGACCATGGACTTCCAAGGAAGATACATGGACTCCCAGGGAAGAATGGTC
3a    TGACCATGGACTTCCAAGGAAGATACATGGACTCCCAGGGAAGAATGGTC
      * * * * * * * * * * * * * * * * * * * * * * * * * * * * * * * *   * *   * * * * * * * * * *

1a    GACCCCAGATACTACGACTACTATGGAAGATTCAACGACTATGACCGTTA
1b    GACCCCAGATACTACGACTACTATGGAAGATTCAACGACTATGACCGTTA
2a    GACCCCAGATACTACGACTACTATGGAAGATACAACGACTATGACCGTTA
2b    GATCCCAGGTTCTACGACTACTATGGAAGATACAACGACTATGACCGTTA
2c    GACCCTAGATACTACGACTACTATGGAAGATACAACGACTATGACCGTTA
2d    GACCCCAGATACTACGACTACTATGGACGATTCAACGACTATGACCGTTA
3a    GACCCCAGGTACTACGACTACTATGGAAGATACAACGACTACGACCGTTA
      * *   * *   * *   *   * * * * * * * * * * * * * * *   * * *   * * * * * * * *   * * * * * * *

1a    CTACGGAAGATCCATGTTCAACTACGGCTGGATGATGGACGGTGATAGGT
1b    CTACGGAAGATCCATGTTCAACTACGGCTGGATGATGGACGGTGATAGGT
2a    CTACGGAAGATCCATGTTCAACTACGGTTGGATGATGGACGGTGATAGGT
2b    CTACGGAAGATCCATGTTCAACTACGGCTGGATGATGGACGGTGATAGGT
2c    CTACGGAAGATCCATGTTCAACTACGGCTGGATGATGGACGGTGATAGGT
2d    CTACGGAAGATCCATGTTCAATTACGGCTGGATGATGGACGGTGATAGGT
3a    TTACGGAAGATCCATGTTCAATTACGGCTGGATGATGGACGGTGATAGGT
       * * * * * * * * * * * * * * * * *   * * * * *   * * * * * * * * * * * * * * * * * * * *

1a    ACAACAGATACAACCGATGGATGGACTACCCCGAGAGGTACATGGACATG
1b    ACAACAGATACAACCGATGGATGGACTACCCCGAGAGGTACATGGACATG
2a    ACAACAGATACAACCGATGGATGGACTTCCCCGAGAGGTACATGGACATG
2b    ACAACAGATGCAACCGATGGATGGACTACCCCGAGAGGTACATGGACATG
2c    ACAACAGATACAACCGATGGATGGACTTCCCCGAGAGGTACATGGACATG
2d    ACAACAGATACAACCGATGGATGGACTTCCCCGAGAGGTATATGGACATG
3a    ACAACAGATACAACCGATGGATGGACTACCCAGAGAGGTACATGGACATG
      * * * * * * * *   * * * * * * * * * * * * * * *   * * *   * * * * * * *   * * * * * * * *
```

Figure 5b (cont.)

```
1a    TCTGGCTACCAGATGGACATGTCTGGACGCTGGATGGACATGCAGGGACG
1b    TCTGGCTATCAGATGGACATGTCTGGACGCTGGATGGACATGCAGGGACG
2a    TCTGGCTACCAGATGGACATGTACGGACGCTGGATGGACATGCAGGGACG
2b    TCTGGCTATCAGATGGACATGTACGGACGCTGGATGGACATGCAGGGACG
2c    TCTGGCTACCAGATGGACATGTACGGACGCTGGATGGACATGCAGGGACG
2d    TCTGGCTACCAGATGGACATGTACGGACGCTGGATGGACATGCAGGGACG
3a    TCTGGCTACCAGATGGACATGTACGGACGCTGGATGGACATGCAGGGACG
      ******* ************   **************************

1a    CCACTGCAACCCGTATAGCCAATGGATGATGTACAACTACAACAGACACG
1b    CCACTGCAACCCGTACAGCCAGTGGGGT---TACAACTATAATAGACACG
2a    CCACTGCAACCCGTATAGCCAATGGATGATGTACAACTACAACAGACACG
2b    CCACTGCAACCCGTATAGCCAATGGATGATGTACAACTACAACAGACACG
2c    CCACTGCAACCCGTATAGCCAATGGATGATGTACAACTACAACAGACACG
2d    CCACTGCAACCCGTACAGCCAATGGATGATGTACAACTACAACAGACACG
3a    CCACTGCAACCCGTACAGCCAATGGATGATGTACAACTACAACAGACACG
      *************** ***** ***        ******* ** *******

1a    GTTACTATCCCAACTACTCCTACGGCCGCCATATGTTCTACCCGGAGAGA
1b    GTTACTATCCCAACTACTCCTACGGCCGTCATATGTTCTACCCAGAAAGA
2a    GTTACTATCCCAACTACTCCTACGGCCGCCATATGTTCTACCCGGAGAGA
2b    GTTACTATCCCAACTACTCCTACGGCCGCCATATGTTCTACCCGGAGAGA
2c    GTTACTATCCCAACTACTCCTACGGCCGCCATATGTTCTACCCGGAGAGA
2d    GTTACTATCCCAACTACTCCTACGGCCGCCATATGTTCTACCCGGAGAGA
3a    GTTACTATCCCAACTACTCCTACGGCCGTCATATGTTCTACCCGGAGAGA
      **************************** ************** ** ***

1a    TGGATGGACATGTCTAACTACTCCATGGACATGTACGGACGTTACATGGA
1b    TGGATGGACATGTCTGGTTATCAGATGGATATGCAAGGTCGCTATATGGA
2a    TGGATGGACATGTCTAACTACTCCATGGACATGTACGGACGTTACATGGA
2b    TGGATGGACATGTCTAACTACTCCATGGACATGTACGGACGTTACATGGA
2c    TGGATGGACATGTCTAACTACTCCATGGACATGTACGGACGTTACATGGA
2d    TGGATGGACATGTCTAACTACTCCATGGACATGTACGGACGTTACATGGA
3a    TGGATGGACATGTCTAACTACTCCATGGACATGTACGGACGTTACATGGA
      ***************  **    ***** *** ** ** ** *****

1a    CAGGTGGGGACGTTACTGCAACCCGTTCTCCCAGTACATGAATTACTATG
1b    CAGATGGGGCCGTTATTGCAACCCGTTCTCCCAGTACATGAATTATTATG
2a    CAGGTGGGGACGTTACTGCAACCCGTTCTACCAATTCTACAACCACTGGA
2b    CAGGTGGGGACGTTACTGCAACCCGTTCTACCAATTCTACAACCACTGGA
2c    CAGGTGGGGACGTTACTGCAACCCGTTCTACCAATTCTACAACCACTGGA
2d    CAGGTGGGGACGTTACTGCAACCCGTTCTACCAATTCTACAACCACTGGA
3a    CAGGTGGGGACGTTACTGCAACCCGTTCTATCACTATTACAACCACTGGA
      *** ***** ***** *************  ** *      ** * *

1a    GCAGATACTGGAACTACCCCGGGTACAACAACTATTATTACAGCAGAAAC
1b    GCAGATACTGGAACTACCCCGGATATAACAGCTATTATAACAGCAGGAAT
2a    ACCGCTACGGCAACTACCCCGGGTACTATAACTACTACTACA--------
2b    ACCGCTACGGCAACTACCCCGGGTACTATAACTACTACTACA--------
2c    ACCGCTACGGCAACTACCCCGGGTACTATAACTACTACTACA--------
2d    ACCGCTACGGCAACTACCCCGGGTACTATAGCTACTACTACA--------
3a    ACCGCTCCGGCAACAACCCCGGGTACTATAGCTACTACTACA--------
      *  *   *  *** ********* ** ** ** ** ***
```

Figure 5b (cont.)

```
1a    ATGTACTACCCAGAAAGATACTTCGATATGTCTAACTGGCAGATGGATAT
1b    ATGTTCTACCCAGAAAGATACTTCGATATGTCTAACTGGCAGATGGATAT
2a    -TGTACTACCCGGAAAGATATTTCGACATGTCTAACTGGCAGATGGATAT
2b    -TGTACTACCCGGAAAGATATTTCGGCATGTCTAACTGGCAGATGGATAT
2c    -TGTACTACCCGGAAAGATATTTCGACATGTCTAACTGGCAGATGGATAT
2d    -TGTACTACCCAGAGAGATACTTCGACATGTCTAACTGGCAGATGGATAT
3a    -TGTACTACCCAGAGAGATACTTCGACATGTCTAACTGGCAGATGGATAT
      ***  ****** ** ***** ****   **********************

1a    GCAGGGACGCTGGATGGATAACCAAGGACGCTACTGCAGCCCCTATTGGA
1b    GCAGGGACGCTGGATGGATAACCAAGGACGTTACTGTAGCCCTTATTGGA
2a    GCAGGGACGCTGGATGGATATGCAGGGACGCTACTGCAGCCCCTATTGGT
2b    GCAGGGACGCTGGATGGATATGCAGGGACGCTACTGCAGCCCCTATTGGT
2c    GCAGGGACGCTGGATGGATATGCAGGGACGCTACTGCAGCCCTTATTGGT
2d    GCAGGGACGCTGGATGGATATGCAGGGACGCTACTGCAGCCCCTATTGGT
3a    GCAGGGACGCTGGATGGATATGCAGGGACGCTACTGCAGCCCCTATTGGT
      ******************   ** ***** ***** ***** ******

1a    ACAACTGGTATGGCAGACATATGTACTACCCGTACCAGAACAATTATTTC
1b    ACAACTGGTATGGCAGACAGATGTACTACCCGTACCAGAACAATTATTTC
2a    ACAACTGGTATGGCAGACATATGTACTACCCCTACCAGAACTACTATTGG
2b    ACAACTGGTATGGCAGACATATGTACTACCCCTACCAGAACTACTATTGG
2c    ACAACTGGTATGGCAGACAGATGTACTACCCCTACCAGAACTACTATTGG
2d    ACAATTGGTATGGCAGACATATGTACTACCCCTACCAGAACTACTATTGG
3a    ACAACTGGTATGGCAGACAGATGTACTACCCCTACCAGAACTACTATTGG
      ****  ************* ********** ********* *  ****

1a    TACGGCCGTTATGACTATCCCGGAATGGACTATTCCAACTATCAGATGGA
1b    TATGGCCGTTATGACTATCCCGGAATGGACTATTCCAACTATCAGATGGA
2a    TACGGCCGTTATGACTATCCCGGGATGGACTATTCCAACTGGCAGATGGA
2b    TACGGCCGTTATGACTATCCCGGGATGGACTATTCCAACTGGCAGATGGA
2c    TACGGCCGTTATGACTATCCCGGAATGGACTATTCCAACTATCAGATGGA
2d    TACGGCCGTTATGACTATCCCGGGATGGACTATTCCAACTGGCAGATGGA
3a    TACGGCCGATGGGACTATCCCGGAATGGACTATTCCAACTGGCAGATGGA
      ** *****  *         ******* ****************  *******

1a    CATGCAGGGACGCTATATGGACCAATACGGAATGAACGACTATTACTATT
1b    CATGCAGGGACGCTATATGGACCAATACGGAATGAACGACTATTGCTATT
2a    TATGCAGGGACGCTGGATGGATATGCAAGGGCGATACATGGATTATCCCT
2b    TATGCAGGGACGCTGGATGGACATGCAAGGGCGATACATGGATTATCCCT
2c    TATGCAGGGACGATATATGGACATGCAAGGGCGATACATGGATTATCCCT
2d    TATGCAGGGACGCTGGATGGATATGCAAGGGCGATACATGGATTATCCCT
3a    TATGCAGGGACGCTGGATGGACATGCAGGGACGATACATGGACCCCTGGT
       **********  *  *****     *  **   **   *        *

1a    AA
1b    AAAT-ATTAAATAGTTTAG
2a    ATA---ATTATTACAACTGGTATTAA
2b    ATA---ATTATTACAACTGGAATCACTAG
2c    ATA---ATTATTACAACTGGAATCACTAGTGA
2d    ATA---ATTATTACAACTGGAATCACTAGGTGA
3a    GGATGAACGACTCCTACTACAATAACTACTACAATTAA
```

MDMSNYMDMYGRYMDRWG

Figure 13

```
cat atg gga tcc atg aac cgc ttt atg aat cgt tat cgc ccg atg
ttt aac aat atg tat agc aac atg tat cgc ggc cgt tat cgc ggt
atg atg gaa ccg atg tcg cgc atg acc atg gat ttc cag ggc cgt
tac atg gat agc cag ggg cgc atg gtg gac ccg cgc tat tac gac
tat tac ttt aac gac tac gat cgt tat tac ggc cgt agc atg ttc
aac tat ggt tgg atg atg gat ggc gat cgc tat aat cgt tat aat
cgc tgg atg gac tat cca gaa cgc tat atg gat atg agc ggt tac
cag atg gat atg tcg ggc cgt tgg atg gac atg caa ggt cgc cat
tgt aac ccg tat tcc cag tgg atg atg tat aac tac aat cgt cat
ggt tac tat cca aac tac tct tat ggc cgc cac atg ttt tac ccg
gag cgt tgg atg gat atg agt aac tat agc atg gat atg tac ggt
cgc tac atg gat cgc tgg ggt cgt tac tgc aat ccg ttc tcg cag
tat atg aac tac tac ggc cgc tat tgg aat tac ccg ggt tat aac
aat tat tat tac agc cgc aac atg tat tac ccg gaa cgt tac ttt
gat atg agc aac tgg cag atg gac atg cag ggc cgt tgg atg gat
aat cag ggg cgc tat tgc tcc ccg tat tgg aat aac tac ggt cgc
cac atg tat tac cca tac caa aac aac tat ccg ttt tac ggc cgt
tat gac tac ccg ggc atg gat tat agc aat tac caa atg gat cag
ggg cgc tat atg gat cag tac ggt atg aac gat tat tac tat taa
tgt aca aga tcc aga tct aag ctt ggt acc acg cgt gcg cgc tga
tcc ggc tgc taa

US 7,314,735 B2

IDENTIFICATION AND CHARACTERIZATION OF REFLECTIN PROTEINS FROM SQUID REFLECTIVE TISSUES

PRIORITY

This application claims priority to U.S. Provisional Application 60/549,733, filed Mar. 2, 2004, herein incorporated by reference in its entirety.

STATEMENT REGARDING FEDERALLY SPONSORED RESEARCH

This invention was made in part with Government support under Grant No. IBN 0211673, and AI50661 awarded by the National Institutes of Health. The Government may have certain rights in this invention.

FIELD OF THE INVENTION

The invention relates generally to a new family of proteins that compose a subcellular structure that confers reflectivity to squid tissues. More specifically, the invention relates to squid reflectin proteins and active portions and repeat units thereof.

BACKGROUND OF THE INVENTION

The biological world is an arena of nanofabrication, one that can be tapped for information about constraints on the design and production of small-scale materials. Among the most intricate of natural nanoscale materials are those that modulate light, such as the lenses, irises, and reflectors of animals (Vukusic, et al. 2003 *Nature* 424, p. 852). Reflective tissues are prevalent across the animal kingdom, being particularly conspicuous in species that live in the visually homogeneous pelagic environments of the ocean. In these habitats, reflectors often function in camouflaging by modulating incident sunlight or bioluminescence (Johnsen, et al. *Proc. Royal Soc.* London. B 2001, 269, p. 243; Johnsen, et al. *Limnol. Oceanogr.* 2003, 48, p. 1277). Reflectivity in animal tissues is achieved by the deposition of flat, insoluble, structural platelets of high refractive index that alternate in layers with materials of low refractive index. This arrangement creates thin-film interference, that results in reflection of some or all of the incident light (Land, et al. *Prog. Biophys. Molec. Biol.* 1972, 24, p. 75). In aquatic animals, reflector platelets are most often composed of purine crystals, particularly guanine and hypoxanthine (Denton, et al. *Proc. Roy. Soc. Lond. A.* 1971, 178, 43). In contrast, cephalopod reflector platelets do not contain these purines and studies of their biochemical and biophysical characteristics have suggested that they are composed of protein (Cooper, et al. *Cell Tissue Res.* 1990, 259, p. 15). However, the composition of cephalopod reflector platelets has never been definitively characterized (Cloney, et al. *Amer. Zool.,* 1983, 23, p. 581). Each of the cited references herein are incorporated by reference in its entirety.

SUMMARY OF THE INVENTION

One embodiment provides for an isolated reflectin polypeptide having a sequence with at least about 75% identity to SEQ ID NO:2, including 85% identity to SEQ ID NO:2. In some embodiments, the polypeptide has a predicted isoelectric point above 8.0.

Other embodiments provide for an isolated polynucleotide encoding a reflectin polypeptide, the polynucleotide having a sequence with at least about 65% identity to SEQ ID NO:1, including 77% identity and 85% identity.

Other embodiments provide for an isolated polypeptide having and least one and no more than four repeats of an amino acid sequence having the motif $[\alpha(X)_{4/5}MD(X)_5MD(X)_{3/4}]$, wherein $\alpha$ is MD, FD, or null; X represents any amino acid; the subscripted numbers represent the number of amino acids at that position; and the slash represents "or." In some embodiments the amino acid sequence is selected from the group consisting of: SEQ ID NOs: 15-30 and any combination thereof. In other embodiments the isolated polpeptide has an activity of a reflectin protein.

Other embodiments provide for an isolated polypeptide having six or more repeats of an amino acid sequence having the motif $[\alpha(X)_{4/5}MD(X)_5MD(X)_{3/4}]$, wherein $\alpha$ is MD, FD, or null; X represents any amino acid; the subscripted numbers represent the number of amino acids at that position; and the slash represents "or." In some embodiments the amino acid sequence is selected from the group consisting of: SEQ ID NOs:15-30, and any combination thereof.

Other embodiments provide for a biomimetic reflective material having a first component, the first component having at least one polypeptide selected from (a) a reflectin polypeptide; (b) a polypeptide having at least one and not more than four repeat units of a reflectin polypeptide; (c) a polypeptide having at least six repeat units of a reflectin polypeptide; (d) an active or functional homologue or recombinant form of any of (a) through (c); and (e) any combination of (a) through (d); the first component being in combination with at least a second component compatible with the first component, such that the combination forms a biomimetic reflective material. In some embodiments, the biomimetic reflective material includes a metal ion. In other embodiments, the material has at least a first and a second refractive state, wherein the material in the first refractive state has a refractive index that is different from a refractive index of the material in the second state.

Other embodiments provide for a method of producing a biomimetic reflective material, by providing a first component having at least one polypeptide (a)-(e) where (a) a reflectin polypeptide; (b) a polypeptide having at least one and not more than four repeat units of a reflectin polypeptide; (c) a polypeptide having at least six repeat units of a reflectin polypeptide; (d) an active or functional homologue or recombinant form of any of (a) through (c); and (e) any combination of (a) through (d); combining the first component with at least a second component to form a biomimetic reflective material. In some embodiments, the second component is a metal, an ion, a polymer, a fabric, a crystal, a fiber, a plastic or any other suitable material.

Further embodiments include a method of producing a biomimetic reflective material, by causing expression in a cell, of at least one polypeptide selected from: (a) a reflectin polypeptide; (b) a polypeptide having at least one and not more than four repeat units of a reflectin polypeptide; (c) a polypeptide comprising at least six repeat units of a reflectin polypeptide; (d) an active or functional homologue or recombinant form of any of (a) through (c); and (e) any combination of (a) through (d); using the cell or a fragment or extract thereof in producing a biomimetic reflective material. In some embodiments, the cell is a plant cell, a bacterial cell; a fungal cell, or an animal cell.

Further embodiments provide for a method of modifying a refractive index of a reflectin, by: providing a reflectin polypeptide in a composition compatible with a metal ion, wherein the composition has a first refractive index in absence of the metal ion; adding the metal ion to the composition, wherein the composition has a second refractive index in presence of the metal.

BRIEF DESCRIPTION OF THE DRAWINGS

FIG. 4. Amino acid alignments, comparisons, and compositions of the derived amino acid sequences for *E. scolopes* reflecting and *L. forbesi* mrrp1 (Lf). (A) Alignment (Clustal V) of reflectin proteins 1a-3a with *L. forbesi* mrrp1. 1a is SEQ ID NO:2, 1b is SEQ ID NO:4, 2a is SEQ ID NO:6, 2b is SEQ ID NO:8, 2c is SEQ ID NO:10, 3a is SEQ ID NO:12, and Lf is SEQ ID NO:14. The black bars are located above the tryptic peptides that were sequenced (SEQ ID NOs: 31-33); *, residues are identical in all sequences in the alignment; colon (:), are conserved substitutions present in the alignment; period (.), are semi-conserved substitutions present in the alignment. (B) Pairwise comparison of the reflectins and *L. forbesi* mrrp1 expressed as percent identity. (C) Amino acid composition of representatives of the *E. scolopes* reflectin family. # is the number of times each amino acid occurs in each protein; % is the percent of each amino acid out of the total number of amino acids that occur in each protein.

FIGS. 5a and 5b. FIG. 5a is a ClustalW alignment of *E. scolopes* reflectins 1a, 2a and 3a and *L. forbesi* mrrp1 nucleotide sequences (SEQ ID NOs: 1, 5, 11 and 13). These sequences share 62.5% identity. FIG. 5b is a ClustalW alignment of *E. scolopes* reflectins 1a, 1b, 2a, 2b, 2c, 2d, and 3a nucleotide sequences (SEQ ID NOs: 1, 3, 5, 7, 45 and 9).

FIG. 13 is the nucleotide sequence of the Reflectin 1a sequence using *E.coli* codon usage (SEQ ID NO:44) to produce the polypeptide sequence of Reflectin 1a (SEQ ID NO:2).

DETAILED DESCRIPTION OF THE PREFERRED EMBODIMENTS

Figure 1:
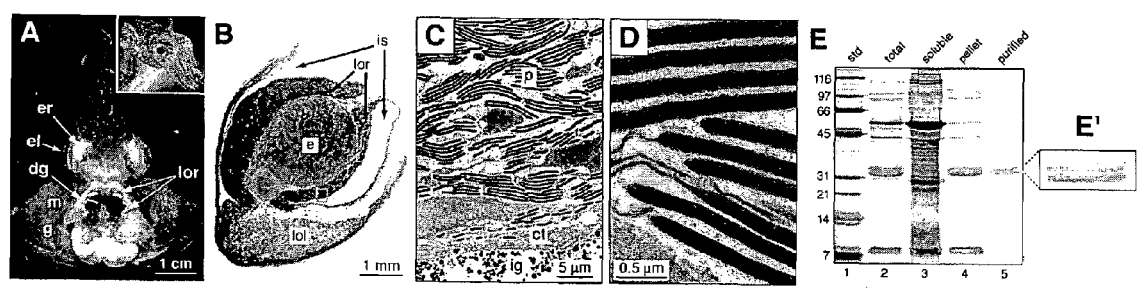
FIG. 1. Reflective tissues in *Euprymna scolopes*. (A) The locations of reflective (dg, digestive gland; er, eye reflector; lor, light organ reflector; m, mantle) and non-reflective (el, eye lens; g, gill) tissues of *E. scolopes* are revealed by a ventral dissection of an adult animal; inset, an adult animal. (B) A light micrograph of a cross section (location at orange line in panel A) of the light organ. The central epithelium (e) is surrounded by the reflector (lor), that is in turn surrounded by ink sac diverticula (is). Lens tissue (lol) is located on the ventral surface of the light organ. (C) Transmission electron micrograph (TEM) of the boxed area in B. Stacks of electron-dense reflector platelets (p) abut connective tissue (ct) and the ink sac with its secreted ink granules (ig). (D) Higher magnification TEM of the light organ reflector (LOR) platelets. (E) Silver-stained SDS-PAGE gel of protein extracts from LORs. LOR tissue extracts were prepared as described in the Examples. lane 1, molecular mass markers (std) expressed in kDa; lane 2, total homogenate of LOR (total); lane 3, supernatant fraction of LOR extracted in PBS (soluble); lane 4, supernatant of pellet from PBS-extracted LOR re-extracted with 2% SDS (pellet); lane 5, purified reflectins (purified). 5 µg of protein loaded in lanes 2-4 samples; 3 µg loaded in lane 5. (E') Higher magnification of reflectin bands, showing the presence of 3 protein species.

A family of reflectin proteins is described herein; the proteins are deposited in flat, structural platelets in reflective tissues of the squid *Euprymna scolopes*. These proteins are encoded by at least six genes in three subfamilies and have no reported homologues outside of squids. Reflectins possess 5 repeating domains that are remarkably conserved among members of the family. The proteins have a highly unusual composition with four relatively rare residues (tyrosine, methionine, arginine, and tryptophan) comprising ~57% of a reflectin, and several common residues (alanine, isoleucine, leucine, and lysine) occurring in none of the family members. These protein-based reflectors in squids provide a striking example of nanofabrication in animal systems.

Identification of the reflectin proteins associated with reflective tissues of *E. scolopes* has led to data on amino acid composition and sequence that are unique to electron dense reflective tissues of this species. Analysis of these sequences has shown the composition of the protein to contain a high percentage of arginine, tyrosine, methionine, and tryptophan residues. Within each of the identified reflectin proteins there exists five repeating domains that show strong sequence conservation. Repeat domains have been the hallmark of many structural proteins identified throughout nature, and typically represent the catalytic, or functional, element of the protein. In an effort to elucidate the nature of the reflectin repeat peptides (RRP), the RRP from the third repeat region from the reflectin 1a protein (FIG. 6) was studied, having the sequence MDMSNYMDMYGRYMDRWG (SEQ ID NO:15). The data show that the RRP has reflective activity and also show the secondary structure and properties of the protein in solution and in the presence of metal ions. The data suggest that the RRP can be used in lieu of the whole protein for the same uses.

In vivo, it is believed that the reflecting platelets function by acting as Bragg reflectors with alternating regions of high and low index of refraction materials. The generation of a proteinaceous matrix with a high refractive index is dependent on a number of variables and includes amino acid composition, concentration and crystallinity of the material, and addition of materials such as inorganic metals or in vivo associated ligands/proteins that can complex with the reflectin proteins. In addition, there may exist molecular level organization of the reflectin protein to optimize the overall effective refractive index. These variables are explored through structural and optical characterization of the RRP. Investigation into the discovery of a protein-based reflective material represents a paradigm shift in how structural coloration is viewed. Both the overall bulk materials and microstructure contribute to the reflective ability of these structures, and these mechanisms work cooperatively. While static reflection characterized in this work differs mechanistically from that of dynamic iridophore tissues, the latter most likely derives its function through molecular manipulation of a similar bulk material described herein. The ability to rearrange substructures, alter binding of inorganics and associated proteins, and/or control crystallinity of the bulk can represent some ways in which dynamic reflection can be controlled. It is likely that the overarching principles and structure in both dynamic and static systems are related and should be represented by a conservation of amino acid sequences of the proteins from different species (see also Crookes, et al. 2004 *Science* Vol. 303, page 235, incorporated by reference in its entirety).

Reflective Tissues

The Hawaiian bobtail squid *Euprymna scolopes* (Cephalopoda:Sepiolidae; FIG. 1A) is similar to other cephalopod species that have been studied in having both variably reflective tissues, such as the skin of the mantle, and statically reflective tissues, such as those associated with the eye, digestive gland, and light organ. The reflector of the bibbed light organ is a particularly well developed tissue (FIG. 1A-D) that modulates the luminescence produced by a population of the symbiotic bacterium *Vibrio fischeri*. On each side of the adult light organ, symbiont-containing epithelial tissue comprises a core that is surrounded by the thick silvery reflector. Together with a muscle-derived lens, these dioptrics function to direct the bacterial luminescence ventrally. Consistent with reflectors in other animals, the light organ reflector (LOR) tissue is composed of a thick layer of platelets (FIG. 1C-D).

The Reflectin Proteins

The seven novel reflectin proteins from squid, and their nucleotide sequences are disclosed herein (see the Examples). Thus, some embodiments of the present invention include one or more novel reflectin polypeptides and/or polynucleotides encoding such polypeptides.

In some embodiments, the reflectin polypeptide is at least about 72% identical to at least one of the reflectin proteins from *E. scolopes* (SEQ ID NOs: 2, 4, 6, 8, 10, 12 and 47), including but not limited to about 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100%. In further embodiments, the polypeptide is at least about 75% identical to at least one of the reflectin proteins from *E. scolopes* (SEQ ID NOS: 2, 4, 6, 8, 10, 12 and 47). In further embodiments, the polypeptide is a functional reflectin. In some embodiments, by functional is meant that a polypeptide has the function or activity of a reflectin. In further embodiments, a functional polypeptide shows a golden yellow color upon SDS-PAGE electrophoresis and silver staining. In further embodiments, a functional polypeptide acts as a BRAGG reflector. In further embodiments, a functional polypeptide has a high refractive index. In further embodiments, a functional polypeptide can complex with inorganic metals. In further embodiments a functional polypeptide is active when it has at least one of the above activities and/or qualities.

Further embodiments are polynucleotides that encode the polypeptide recited above. In some embodiments, the polynucleotide is a natural sequence from a squid genome. In further embodiments, the polynucleotide is a derived sequence in which the codon usage for *E. coli* or an alternative organism is used to express a polypeptide that is at least 72.5% identical to any of SEQ ID NOS:2, 4, 6, 8, 10, 12 and 47. In further embodiments, the polynucleotide is at least about 65% identical to the polynucleotide sequence from *E. scolopes* reflectin proteins 1a, 1b, 2a, 2b, 2c and 3a (SEQ ID NOS: 1, 3, 5, 7, 9, 11 and 46). In further embodiments, the polynucleotide is at least about 70% identical, including but not limited to: 75%, 77%, 80%, 85%, 90%, 95%, 97.5%, and 99%. In further embodiments, the polynucleotide sequence encodes an active or functional reflectin protein as described above.

As described herein, each reflectin protein is composed of a series of five repeats (designated RRPs). Thus, further embodiments are polypeptides or corresponding polynucleotide sequences that are engineered or truncated in such a way as to remove one or more of the RRPs. Further embodiments are polypeptides or corresponding polynucleotide sequences that have one or more of the RRP sequences removed internally. This can result in an active or functional polypeptide that simply has fewer repeat units but still retains function.

Reflective Repeat Peptide (RRP)

In some embodiments, the RRP is any amino acid sequence corresponding to the motif $[\alpha(X)_{4/5}MD(X)_5MD(X)_{3/4}]$, wherein $\alpha$ is MD, FD, or null; X represents any amino acid; the subscripted numbers represent the number of amino acids at that position and the slash represents "or." For example $(X)_{4/5}$ means that either four or five amino acids can be at that position, and those four or five amino acids can be any amino acids in any order or combination. Various permutations of the single repeat peptide include SEQ ID NOs: 15-30.

A highly conserved sequence was identified within the RRP motif as shown in Table 1. Thus, in some embodiments, the RRP sequence comprises the motif [MDMQGRY/W] (SEQ ID NO: 48). In further embodiments, the RRP comprises any amino acid sequence corresponding to the motif [MDMQGRY/W] (SEQ ID NO: 48) or any variants with conserved amino acids within that sequence, wherein the last amino acid is either Y or W. The sequence may include other amino acids at the N- or C-terminus, including but not limited to 1, 2, 3, 4, 5, 6, 7, 8, 9, 10, 11, 12, 13, 14, 15, and 20 additional residues. In some embodiments, the amino acids at the N- and/or C-terminus are selected from those in SEQ ID NOs: 15-30.

TABLE 1

| | |
|---|---|
| M S R M T M D F Q G R Y M D S Q G R | SEQ ID NO:16 |
| M D M S G Y Q M D M S G R W M D M Q G R | SEQ ID NO:17 |
| M D M S N Y S M D M Y G R Y M D R W G R | SEQ ID NO:18 |
| M D M S G Y Q M D M Q G R Y M D R W G R | SEQ ID NO:19 |
| F D M S N W Q M D M Q G R W M D N Q G R | SEQ ID NO:20 |
| F G M S N W Q M D M Q G R W M D N Q G R | SEQ ID NO:21 |
| M D Y S N Y Q M D M Q G R Y M D   Q G R | SEQ ID NO:47 |
| M D Y S N W Q M D M Q G R W M D M Q G R | SEQ ID NO:23 |
| M D Y S N Y Q M D M Q G R Y M D M Q G R | SEQ ID NO:24 |
| F D M S N W Q M D M Q G R Y M D Q Y G | SEQ ID NO:25 |
| M D M S N Y S M D M Q G R W M D N Q G R | SEQ ID NO:26 |
| M D M S G Y Q M D M Q G R W M D M Q G R | SEQ ID NO:27 |
| M S R M T M D F Q G R Y M D R W G R | SEQ ID NO:28 |
| F D M S N W Q M D M Q G R Y M D Q Y G R | SEQ ID NO:29 |
| F D M S R M T M D F Q G R Y M D S Q G R | SEQ ID NO:30 |

Because the RRPs are the functional units of the protein, any modifications to the protein sequence that conserve at least one of the RRP sequences can result in an active or functional polypeptide. Likewise, any modifications to a polynucleotide encoding the protein, when such modifications conserve at least one RRP sequence, results in a polynucleotide encoding an active or functional polypeptide. Thus, a further embodiment is any mutated form of the polypeptides and/or polynucleotides that results in at least one conserved RRP within the sequence. Further embodiments include a polypeptide or an encoding polynucleotide, with a sequence that results in a modified RRP that maintains reflective and/or structural characteristics. In some embodiments, permutations and variants any changes that still produce an active reflectin repeat peptide. In some embodiments, the variants still conform to the formula $[\alpha(X)_{4/5}MD(X)_5MD(X)_{3/4}]$, wherein $\alpha$ is MD, FD, or null; X represents any amino acid; the subscripted numbers represent the number of amino acids at that position and the slash represents "or." In a further embodiment, the variants have substantially the sequences of SEQ ID NOs: 15-30 and SEQ ID NO:47 with one or more substitutions, insertions or deletions that conform to either the formula or one of the RRPs described herein or a like amino acid at the equivalent position.

A further embodiment is an RRP that comprises the formula $[\square(X)4/5MD(X)5MD(X)3/4]$, including but not limited to SEQ ID NOs: 15-30 as follows:

| | |
|---|---|
| MSRMTMDFQGRYMDSQGR, | (SEQ ID NO:16) |
| MDMSGYQMDMSGRWMDMQGR, | (SEQ ID NO:17) |
| MDMSNYSMDMYGRYMDRWGR, | (SEQ ID NO:18) |
| MDMSGYQMDMQGRYMDRWGR, | (SEQ ID NO:19) |
| FDMSNWQMDMQGRWMDNQGR, | (SEQ ID NO:20) |
| FGMSNWQMDMQGRWMDNQGR, | (SEQ ID NO:21) |
| MDYSNYQMDMQGRYMDQYG, | (SEQ ID NO:22) |
| MDYSNWQMDMQGRWMDMQGR, | (SEQ ID NO:23) |
| MDYSNYQMDMQGRYMDMQGR, | (SEQ ID NO:24) |
| FDMSNWQMDMQGRYMDQYG, | (SEQ ID NO:25) |
| MDMSNYSMDMQGRWMDNQGR, | (SEQ ID NO:26) |
| MDMSGYQMDMQGRWMDMQGR, | (SEQ ID NO:27) |
| MSRMTMDFQGRYMDRWGR, | (SEQ ID NO:28) |
| FDMSNWQMDMQGRYMDQYGR, and | (SEQ ID NO:29) |
| FDMSRMTMDFQGRYMDSQGR. | (SEQ ID NO:30) |

Alternative forms of the RRPs that are still active can be produced using these known sequences and substituting amino acids at equivalent positions or producing chimera of the known peptides. For example, the tryptophan at position 6 of SEQ ID NO:23 can be substituted for the tyrosine at position 6 of SEQ ID NO:22. In addition, any amino acids that have the same properties can be substituted. Further, an amino acid at position 2 can be added to any RRP peptides as long as the peptide still conforms to the formula. Other substitutions can be made as long as they conform generally to the formula and still result in an active polypeptide. In one embodiment, the RRP is MDMSNYMDMYGRYMDRWG (SEQ ID NO:15).

A further embodiment is a polypeptide having, and/or a polynucleotide sequence encoding, one or more of the functional repeat units for the reflectin proteins. In some embodiments, the polypeptide includes 1, 2, 3, or 4 RRPs. The RRPs can be any combination or permutation of those provided in SEQ ID NOS: 15-30 and can contain, for example 2 copies of SEQ ID NO:15, one copy of SEQ ID NO:16 and one copy of SEQ ID NO:17. In some embodiments, the polypeptide has four copies of SEQ ID NO:15.

In some embodiments, the polynucleotide has one or more copies of any combination of the functional repeat units as described above. In some embodiments, the polynucleotide encodes a polypeptide having one or more copies of the functional repeat units. In an alternative embodiment, the polynucleotide results in one or more separately translated RRPs.

Further embodiments include polypeptides and/or polynucleotides having or encoding five copies of the RRPs in a combination or arrangement that is not found in nature. In other words, the repeats are provided in a combination that, while not produced in nature, still results in one or more active polypeptides.

Further embodiments are polypeptides having, and/or polynucleotide sequences encoding, six or more of the functional repeat units for the reflectin proteins. In some embodiments, the polypeptide includes 6 or more RRPs, including but not limited to: 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 200, 300, 400, and 500. In further embodiments, the number of copies is between about 6 and about 30. In further embodiments, the number of copies is more than 6 but less than about 1000. The RRPs can be any combination or permutation of those provided in SEQ ID NOS:15-30 and/or functional modifications thereof, and can contain, for example, 2 copies of SEQ ID NO:15, one copy of SEQ ID NO:16, one copy of SEQ ID NO:17, two copies of SEQ ID NO:18, and one copy of SEQ ID NO:19, and so on. In some embodiments, the polypeptide includes six or more copies of SEQ ID NO:15.

In some embodiments, the polynucleotide includes six or more copies of any combination of the functional repeat units as described above. In some embodiments, the polynucleotide encodes a polypeptide having six or more copies of the functional repeat units. In alternative embodiments, the polynucleotide results in six or more separately translated RRPs.

The sequences between the RRPs can be any sequence that does not negatively affect the secondary or tertiary structure of the RRP and can contain a promoter region, a stop codon, or an initiation codon. Thus, it is to be understood that the polynucleotide for the RRP protein can be expressed as a polyprotein containing two or more RRPs or can be expressed as multiple RRP proteins.

Methods of Expressing Reflectins and/or RRPs

As stated above, the polynucleotide can be expressed as a polyprotein containing one or more RRPs or can be expressed such that each RRP is translated separately and/or transcribed separately. Any promoter can be used that will result in expression in the cell of choice.

In some embodiments, the polynucleotide is provided such that the codon usage for the particular cell results in the polypeptide of choice. For example, the $E.\ coli$ codon usage can be used to produce the polypeptide of SEQ ID NOs: 2, 4, 6, 8, 10, 12, or 15-30 or any variant thereof.

Methods of Purifying Reflectins and/or RRPs

In some embodiments, the reflectin protein or RRP unit is purified and stored in a buffer having 0.2% or more SDS or an equivalent detergent, including but not limited to: 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 3%, 3.5%, 4%, 4.5% and 5%. In further embodiments, the buffer includes SDS at about 0.2 to 2%. In further embodiments, the buffer includes nondetergent sulfobetaine (NDSB) 195, 201, and/or 256 at a concentration of about 0.1 to about 10 M, including but not limited to 9 M, 8 M, 7 M, 6 M, 5 M, 4 M, 3 M, 2 M, 1 M, 0.9 M, 0.8 M, 0.7 M, 0.6 M, 0.5 M, 0.4 M, 0.3 M, and 0.2 M. In further embodiments the buffer includes CHAPS at a concentration of about 0.1 to about 10%, including but not limited to: 0.2%, 0.4%, 0.6%, 0.8%, 1%, 1.2%, 1.4%, 1.6%, 1.8%, 2%, 2.5%, 3%, 3.5%, 4%, 4.5%, 5%, 5.5%, 6%, 6.5%, 7%, 7.5%, 8%, 8.5%, 9%, and 9.5%. In further embodiments, the buffer contains urea at a concentration of about 3M to about 10M, including but not limited to 4M, 5M, 6M, 7M, 8M, and 9M. In some embodiments the buffer includes DMSO at a concentration of from about 60% to about 100%, including but not limited to 70%, 80%, 90%, and 95%. In further embodiments, the buffer includes trifluoroethanol in a concentration of from about 60% to about 100%, including but not limited to: 70%, 80%, 85%, 90%, 95%, 97.5%, and 99%. In further embodiments, the buffer includes EDTA at a concentration of from about 0.2 M to about 3M, including but not limited to 0.3M, 0.4 M, 0.5M, 0.6M, 0.7M, 0.8M, 0.9M, 1M, 1.5M, 1.75M, 2M, 2.5M, and 2.75M. In further embodiments, the buffer includes ammonium acetate and/or ammonium sulfate in a concentration of about 0.2M to about 3M, including but not limited to 0.3M, 0.4M, 0.5M, 0.6M, 0.7M, 0.8M, 0.9M, 1M, 1.5M, 1.75M, 2M, 2.5M, and 2.75M In further embodiments, the buffer contains one or more metal ions added at a concentration of about 10 mM or less, to about 100 mM or more, including but not limited to: 20 mM, 30 mM, 40 mM, 50 mM, 60 mM, 70 mM, 80 mM, and 90 mM. In some embodiments, the metal ions are zinc and/or gold, including but not limited to $ZnSO_4$ and $AuCl_4$.

Methods of Using Reflectins and/or RRPs

Any methods of using proteins that reflect and/or have a high refractive index can be used. Some methods include, but are not limited to: as a reporter protein to characterize transcription of a protein and/or a promoter, in nanostructured supramolecular devices, and for nanofabrication of any type of material, for example reflective biomaterials.

EXAMPLES

In Examples 1-3, a total of 6 different reflectin proteins from the Squid $E.\ scolopes$ were identified and sequenced. Example 4 provides an analysis of the sequence. In Examples 5-12, the smallest active portion of the protein, the Reflectin Repeat Peptide (RRP) is expressed, identified and characterized. In Examples 13-14 various methods for the use of the peptides and proteins are provided.

The specimens of $E.\ scolopes$ were obtained from the shallow reef flats of Oahu, Hi., transported to circulating natural seawater aquaria at the University of Hawaii, and maintained as described in Weis, et al. $Biol.\ Bull.$ 1993, 184, p. 309 (herein incorporated by reference in its entirety). All chemicals were obtained from Sigma-Aldrich (St. Louis, Mo.) unless otherwise noted.

Example 1

Isolation of Reflectin Proteins from $E.\ scolopes$

To enrich for the reflecting, the light organ reflector (LOR) was first homogenized in 50 mM sodium phosphate buffer, pH 7.4, with 0.1 M NaCl (PBS) in a ground glass homogenizer on ice to extract the aqueous soluble fraction. The total homogenate was centrifuged at 20,800×g for 15 min at 4° C. The resulting supernatant was removed. The pelleted material was then washed by repeatedly resuspending it in PBS and centrifuging the resuspension at 20,800×g for 15 min at 4° C. to re-pellet the aqueous-insoluble material. The resulting washed pellet was resuspended in 2% SDS in PBS to extract the SDS-soluble fraction that contained the reflecting. The suspension was then centrifuged, as described above, and the supernatant retained for analyses.

Sodium dodecyl sulfate-polyacrylamide gel electrophoresis (SDS-PAGE) was carried out on a Bio-Rad Mini-Protean II electrophoresis system (Bio-Rad, Hercules, Calif.) under standard SDS-PAGE procedures (modified from Laemmli, *Nature* 227, p. 680). The protein concentrations of all fractions were determined spectrophotometrically.

Extractions of total protein from the *E. scolopes* LOR revealed a set of three abundant polypeptides that resolved between 33-36 kDa on SDS-PAGE and were a characteristic golden-yellow color upon silver staining (FIG. 1E, E'). These polypeptides (reflecting) were not detected in the aqueous soluble fraction of the LOR, but were abundant in the supernatant of the SDS-solubilized pellet, composing ~40% of the proteinaceous component of the LOR.

To determine the approximate concentrations of reflectins in the LOR, the protein concentration of the whole homogenate, PBS-soluble supernatant, and the SDS-soluble fraction of the light organ reflector were each determined. From SDS-PAGE analysis of the SDS-soluble fraction of the LOR, reflectins made up at least about 50% of the total protein in this fraction. This value was used to back-calculate to determine what proportion of the whole homogenate was reflecting.

Example 2

Tissue Localization of Reflectins

To localize the reflecting within the LOR, polyclonal antibodies were generated against gel-purified reflectin proteins (FIG. 1E, lane 5) and used in immunocytochemical and immunoblot analyses.

To generate material for antibody production, the reflectin proteins were purified directly from the SDS-PAGE gel of the LOR proteins. Briefly, the 2% SDS-soluble fraction of light organ reflectors from seven adult animals was applied to a stacking gel without wells. The portion of the gel containing the reflectins was excised from the gel and homogenized in 2% SDS in PBS. The resulting slurry was transferred to a Microcon-100 spin filter (Millipore Corp., Bedford, Mass.) and centrifuged at 3000×g for 10 min at room temperature. An aliquot of the filtrate was resolved on SDS-PAGE, that indicated that the desired proteins had been isolated. The remaining filtrate protein was used in the production of polyclonal antibodies (Covance Research Products, Inc., Denver, Pa.). For western blot analysis, protein extractions of the SDS-soluble pellet of various adult tissues were performed as described above for the LOR. The protein concentration of each extraction was determined spectrophotometrically and SDS-PAGE gels were run according to standard protocol. The companion SDS-PAGE gel was silver stained according to standard procedures. For western blots, proteins were electrophoretically transferred to nitrocellulose membrane (Bio-Rad, Hercules, Calif.). Blots were blocked overnight in 4% milk in 50 mM Tris, 150 mM NaCl, 0.5% Tween 20, pH 7.5 (TTBS). Following this blocking step, blots were incubated for 1 h in a 1:10,000 dilution of antiserum in 1% milk/TTBS. Blots were washed 3 times in 1% milk/TTBS and then incubated for 45 min in a mixture of 1:3000 goat anti-rabbit secondary antibodies conjugated to horseradish peroxidase (Bio-Rad, Hercules, Calif.) and 1:3300 avidin-conjugated horseradish peroxidase to detect biotinylated molecular mass markers (Bio-Rad, Hercules, Calif.). These detection reagents were diluted in 1% milk/TTBS. Detection of cross-reactive bands was achieved by chemiluminescence (ECL chemiluminescence kit, Amersham Biosciences Corp, Piscataway, N.J.).

Immunogold localization by transmission electron microscopy (TEM) was performed as follows: Light microscopy and TEM of squid tissues were performed as described in McFall-Ngai, et al. (*Biol. Bull.*, 1990, 184, p. 296) and Montgomery et al. (*J. Biol. Chem.*, 1992, 267, p. 20999), each of which is herein incorporated by reference in its entirety. Immunocytochemistry at the TEM level was also performed as described in Weis et al (see Example 1) except that anti-reflectin antibodies were used as the primary antibody at a 1:1000 dilution. A 1:50 dilution of goat anti-rabbit IgG conjugated to 15-nm gold spheres (Ted Pella, Redding, Calif.) was used as the secondary antibody. To control for nonspecific binding of the secondary antibody, a subset of the grids was incubated with a 1:1000 dilution of preimmune serum. TEM was performed on a JEOL 100 CX transmission electron microscope at the University of Southern California (Los Angeles, Calif.).

Figure 2:
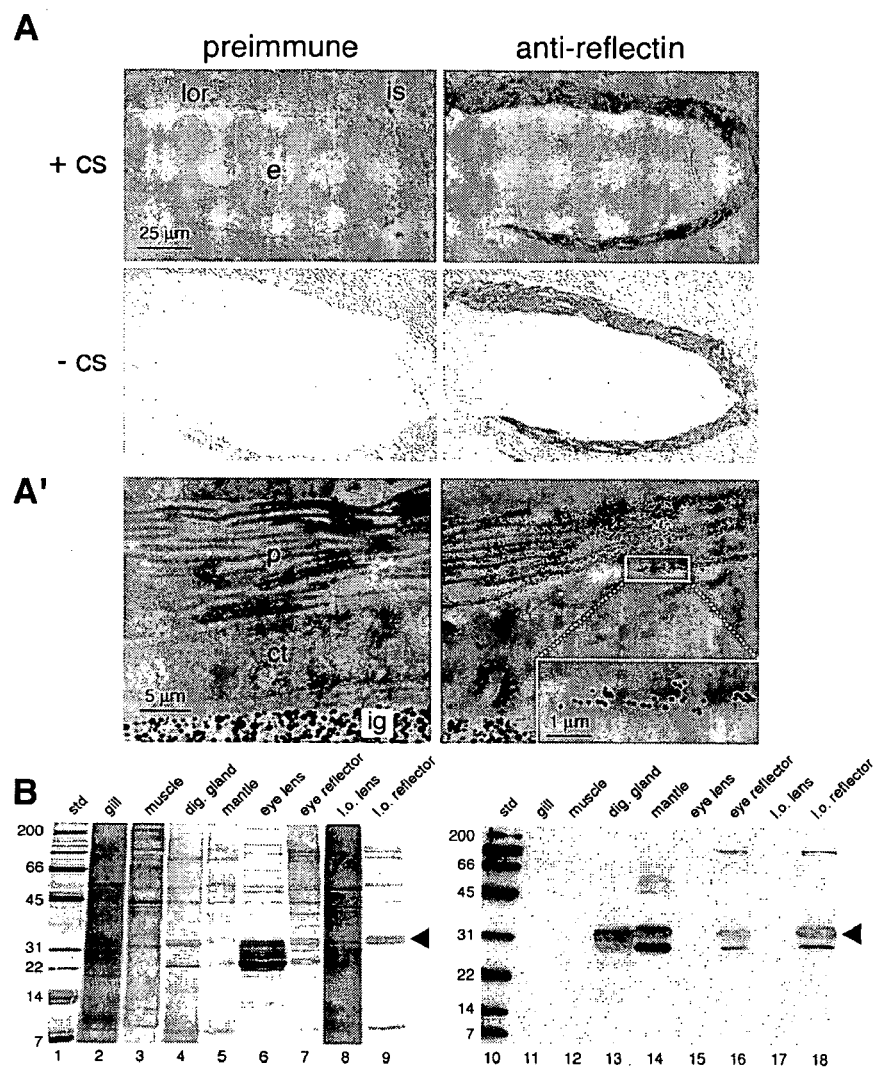
FIG. 2. Localization of reflectins in *E. scolopes*. (A) Immunocytochemistry at the light level. One-µm sections of whole juvenile squid mounted on gelatin-coated glass slides were incubated in either preimmune serum (preimmune) or reflectin antiserum (anti-reflectin). Fifteen-nm gold beads conjugated to goat anti-rabbit IgGs were used as secondary antibodies and sections were silver enhanced (Silver Enhancer Kit; Sigma-Aldrich) to allow detection of the gold beads by light microscopy. The sections were then either counterstained with 1% acid fuchsin (+cs) or left unstained (−cs) and viewed by differential interference microscopy. is, ink sac; lor, reflector; e, central epithelial tissue. (A') Immunocytochemistry at the TEM level. Ultrathin sections of whole juvenile squid mounted on nickel grids were incubated in either preimmune serum or reflectin antiserum. Fifteen-nm gold beads conjugated to goat anti-rabbit IgGs were used as secondary antibodies. Inset, higher magnification showing the labeling of an individual platelet. p, platelets; ct, connective tissue; ig, ink granules. (B) Silver-stained SDS-PAGE (lanes 1-9) and immunoblot analyses (lanes 10-18) of 2% SDS-extracted proteins from pellets of aqueous-buffer extractions of reflective and non-reflective squid tissues; 2.5 µg total protein loaded per lane. std, molecular mass standards in kDa; arrowhead indicates the position on the gels where reflectins resolve. dig. gland, digestive gland; l.o. lens, light organ lens; l.o. reflector, light organ reflector.

The reflectin antibodies strongly recognized the LOR, but not the bacteria-containing epithelium, the ink sac, or lens of the light organ (FIG. 2A). The results of the immunogold localization showed that the reflectins in the LOR were directly associated with the LOR platelets (FIG. 2A') and that no labeling was detected in the surrounding connective tissue or ink granules (FIG. 2A'). Higher magnification TEM images of the LOR demonstrated that the antibodies cross reacted specifically with the electron-dense platelets but not the inter-platelet region (FIG. 2A', inset).

Proteins with similar molecular mass, biochemistry, and antigenicity to LOR reflectins were found in all reflective tissues of *E. scolopes*. Silver-stained SDS-PAGE gels revealed that the characteristic golden-yellow bands at 33-36 kDa were detectable in reflective tissues. In addition, these proteins cross reacted with antibodies to LOR reflectins in western blot analyses (FIGS. 1A, 2B). Cross-reactive bands were also found at other molecular weights (26, 55, and 120 kDa), and corresponding golden-yellow bands were present on the SDS-PAGE gels of these tissues. Because the antibodies were generated from a very discrete region of a gel, and these other bands only occur in reflective tissues, it is likely that the antibodies were cross reacting with other members of the reflectin family or closely related proteins. Cross reactivity was low or undetectable in non-reflective tissues (gills, muscle, eye lens, and light organ lens) (FIG. 2B).

Example 3

Sequencing and Analysis of Reflectins Genes

Figure 3:
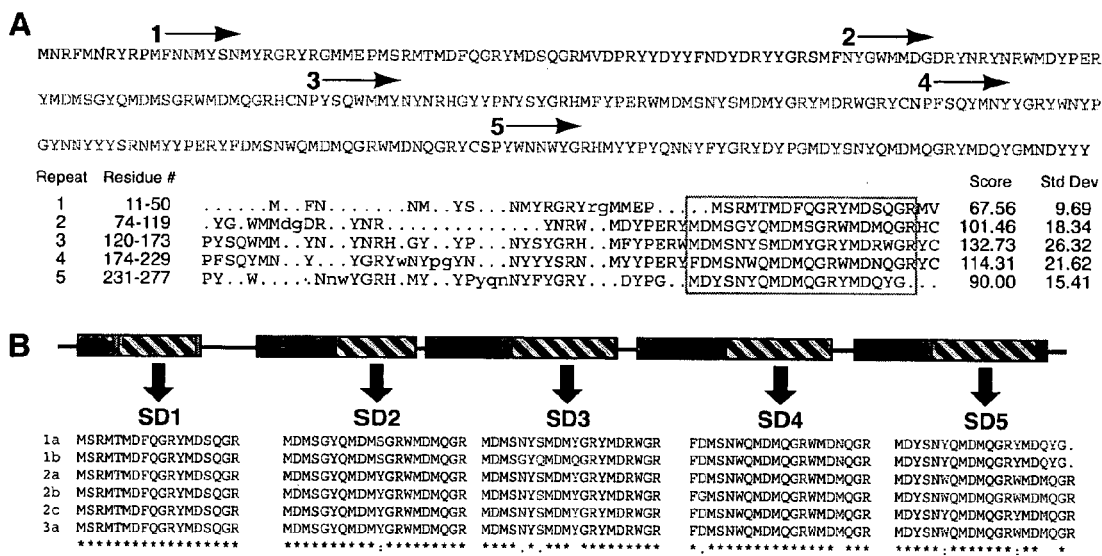
FIG. 3. Reflectins are composed of repeating domains, as predicted by RADAR (Rapid Detection and Alignment of Repeats). (A) Upper panel, the entire amino acid sequence of reflectin 1a with repeat regions indicated in grey and amino acids excluded from the repeats in black (SEQ ID NO:2). Numbers and arrows indicate the number and direction of the repeats. Lower panel, the RADAR output. The fourth repeat was used as the template repeat. Score, "score of each repeat unit when scored against the whole repeat" (RADAR); Std Dev, the number of standard deviations above the mean for shuffled sequences scored against the same profile. (B) Schematic showing the positioning of the repeats (gray boxes) and the conserved subdomains (hatched boxes; SD1-SD5) from a representative reflectin. The subdomains are also outlined in the RADAR alignment in panel 3A (SEQ ID NOs:16-24). The subdomain amino acid alignments among all reflecting are shown under each subdomain. SD1=SEQ ID NO:16, SD2=SEQ ID NO:17, SD3=SEQ ID NO:18 and 19, SD4=SEQ ID NO:20 and 21, and SD5=SEQ ID NOs: 22, 23, and 24.

The sequences of three tryptic peptides (FIG. 3A) from tryptic digestion of gel-purified reflectins (FIG. 1E, lane 5) were used to identify reflectin cDNAs from predicted translations of *E. scolopes* cDNA and EST library clones as described below. The tryptic peptides had ambiguities in them as expressed by an "X" in the following sequences:

SMFNYGWMMDGDR (SEQ ID NO:31), EGYYP-NYSYGR (SEQ ID NO:32), and YFDMSNWQMDMQGR (SEQ ID NO:33).

Protein extracts from light organs were subjected to SDS-PAGE. Reflectin bands were excised from the gel and subjected to trypsin digestion. The resulting tryptic peptides were sequenced by mass spectrometry (Harvard Microchemistry Facility, Cambridge, Mass.). The amino acid sequences of three tryptic peptides were used to screen predicted translations of sequences from cDNA pools constructed from the light organs of juvenile animals (SEQ ID NOs: 31-33). One partial sequence was obtained from this pool, the translation of which contained 2 of the 3 tryptic peptide sequences. This small tryptic peptide sequence had significant similarity (88%) to *Loligo forbesi* 'methionine-rich repeat protein 1' (mrrp1; accession no. CAC86921) (SEQ ID NO:14).

Using the nucleotide sequence of *L. forbesi* mrrp1 (SEQ ID NO:13) for information about possible length and the sequence of the *E. scolopes* partial clone for primer design (Table 2), RACE-PCR (rapid amplification of cDNA ends-polymerase chain reaction) was conducted on an *E. scolopes* light organ cDNA pool to obtain full-length clones. 5' and 3' RACE-PCRs were performed on the clone using the SMART RACE cDNA amplification kit (BD Biosciences Clontech, Palo Alto, Calif.) and primers specific to the cDNA clone (see Table 2; 33F3, 33R2, 33R3, 33R4). First-strand synthesis was performed on 195 ng of light organ mRNA according to the manufacturer's instructions. Both 5' and 3' RACE reaction conditions were as follows: 5 cycles of 94° C. for 30 sec, 72° C. for 3 min; 5 cycles of 94° C. for 30 sec, 70° C. for 30 sec, 72° C. for 3 min; 25 cycles of 94° C. for 30 sec, 68° C. for 30 sec, 72° C. for 3 min. RACE products were run on 1% agarose gels and stained with ethidium bromide according to standard procedures. RACE products were gel-extracted (GeneClean kit, Bio101, Carlsbad, Calif.) and ligated into the pGEM-T easy vector (Promega Corp., Madison, Wis.). Products from the ligation reactions were transformed into *E. coli* DH5alpha and transformants were screened for inserts by blue-white screening on LB-carbenicillin (50 µg/ml) plates containing 0.9 mg IPTG and 800 µg X-gal (Promega Corp, Madison, Wis.). White colonies were further screened by restriction enzyme digestion (EcoRI) to identify those transformants with plasmids that contained appropriately sized inserts. Plasmids from positive colonies were mini-prepped (Qiagen Inc., Valencia, Calif.) and sequenced at the University of Hawaii Biotechnology/Molecular Biology Instrumentation and Training Facility.

TABLE 2

Primers used for RACE-PCR and standard PCR reactions.

| Primer | Primer type | Direction | Sequence (5' to 3') | SEQ ID NO: |
|---|---|---|---|---|
| 33F3 | 3' RACE | forward | CGC CAC TGC AAC CCG TAT AGC CAA TGG | 34 |
| 33R2 | 5' RACE | reverse | CCA ATA GGG GCT GCA GTA GCG TCC | 35 |
| 33R3 | 5' RACE | reverse | GTT GCC GGA GCG GTT CCA GTG GTT GTA A | 36 |
| 33R4 | 5' RACE | reverse | CCC GGG GTA GTT CCA GTA TCT GCC AT | 37 |
| 33AF | standard PCR | forward | ATG AAC CGT TTT ATG AAC AGA TAC CG | 38 |
| 33BF | standard PCR | reverse | ATG AAC CGT TAC ATG AAC CGA TTC CG | 39 |
| 33A1R | standard PCR | reverse | GTA ATA GTC GTT CAT TCC GTA TTG GTC C | 40 |
| 33B1R | standard PCR | reverse | GAG CAA GAC GTT CAA GAA TTT CAG ACG | 41 |
| 33B2R | standard PCR | reverse | CCA GTT GTA ATA ATT ATA GGG ATA ATC C | 42 |
| 33BR | standard PCR | reverse | CCA TGT ATC GTC CCT GCA TGT CCA TCC | 43 |

Genomic DNA extracted from the light organ of a single adult *E. scolopes* was used as a template for PCR reactions to: i) determine whether genes for all 6 cDNAs occur in the genome, or are the result of alternative splicing or allelic differences; and, ii) provide information about gene structure. To amplify reflectin genes from genomic DNA, PCR reactions were carried out using all possible combinations of 2 forward primers: 33AF(SEQ ID NO:38), or 33BF(SEQ ID NO:39) and 4 reverse primers: 33A1 R (SEQ ID NO:40), 33B1R(SEQ ID NO:41), 33B2R(SEQ ID NO:42), and 33BR(SEQ ID NO:43); (see Table 2). Reactions were carried out with 1.5 mM MgCl$_2$, 1 µM each forward and reverse primers, 1 mM dNTPs, and 2.5 U Taq DNA polymerase (Promega Corp., Madison, Wis.). Reaction conditions were as follows: 94° C. for 2 min; 94° C. for 30 sec, 55° C. for 30 sec, 72° C. for 1.5 min for 35 cycles; 72° C. for 5 min. PCR products were cloned and sequenced as outlined above for RACE products.

In addition to reflectin gene sequences obtained from light organ cDNA and genomic DNA, sequences were obtained from an EST database being constructed from light organ cDNA libraries of juvenile animals.

All six full-length reflectin sequences contained stop codons followed by polyadenylated tails, that demonstrates that there was no genomic DNA contamination. Accession numbers for the reflectins can be found in Table 3.

To produce the cDNA pool, RNA was isolated from the light organs from juvenile *E. scolopes* that were dissected, placed in RNAlater (Ambion, Inc., Austin, Tex.), and stored at −20° C. Total RNA was extracted as follows: 80 juvenile light organs were homogenized in 600 µl TriPure Isolation Reagent (Roche Applied Sciences, Indianapolis, Ind.) for 30 min on ice in a ground glass homogenizer. The homogenate was incubated for 5 min at room temperature, and then 120 µl of chloroform was added to the homogenate. The mixture was allowed to stand for an additional 10 min at room temperature, and then centrifuged at 12,000×g for 15 min at 4° C. The upper aqueous phase was transferred to a new tube and 300 µl of isopropanol was added. This mixture was incubated for 7 min at room temperature to allow precipitation of total RNA and then centrifuged at 10,800×g for 10 min at 4° C. The supernatant was discarded and the RNA pellet was washed once with 75% ethanol. The pellet was air dried and was then resuspended in 50 µl of RNase-free water. The resuspension was then incubated at 55° C. for 15 min and assessed for quantity and purity spectrophotometrically. mRNA was extracted from total RNA using the MPG mRNA Purification Kit (CPG, Lincoln Park, N.J.) according to the manufacturer's instructions. mRNA was quantified, assessed for purity spectrophotometrically, and resolved on a 1% agarose gel to confirm that the RNA was not degraded.

Genomic DNA was extracted from one adult light organ reflector using the portion of the MasterPure Complete DNA and RNA Purification Kit (Epicentre, Madison, Wis.) designed to isolated the DNA. During the extraction, the sample was treated with 5 µg RNase A to digest single-stranded RNAs. The DNA was quantified and assessed for purity spectrophotometrically.

TABLE 3

Comparison of predicted protein characteristics of reflectins 1a-3a and *L. forbesi* mrrp1 (Lf).

|    | Accession number | # residues | molecular mass (kDa) | pI   | SEQ ID NO |
|----|------------------|------------|----------------------|------|-----------|
| 1a | AY294649         | 283        | 36.7                 | 8.84 | 2         |
| 1b | AY294650         | 282        | 36.2                 | 8.82 | 4         |
| 2a | AY294652         | 283        | 36.7                 | 8.84 | 6         |
| 2b | AY294653         | 284        | 37.0                 | 8.80 | 8         |
| 2c | AY294654         | 284        | 37.2                 | 8.81 | 10        |
| 3a | AY294651         | 288        | 37.6                 | 8.81 | 12        |
| Lf | CAC86921         | 264        | 32.8                 | 7.61 | 14        |

\# residues, number of total amino acids;
pI, predicted isoelectric point.

Example 4

Analysis of Reflectin Sequences and Homologies

RACE-PCR conducted on light organ cDNA pools using reflectin primers (Table 2) identified six similar reflectin cDNAs (FIG. 1; Table 3), suggesting that several genes encoding reflecting were expressed in the light organ. Sequencing of PCR products from the amplification of genomic DNA provided evidence that all six reflectin genes amplified from the cDNA pools are represented in the genome of a single individual. None of the reflectin genes amplified from genomic DNA possessed introns. Only one entry in the nucleotide databases had similarity to the *E. scolopes* reflecting, a gene sequence from the European squid *Loligo forbesi* (Weiss et al. NCBI accession number CAC86921, 2002) that encodes 'methionine-rich repeat protein 1' (FIG. 1, A and B; Table 3) (accession no. CAC86921). However, there was no known function for *L. forbesi* mrrp 1, and this protein was less than 72.5% identical to any of the *E. scolopes* sequences, while the reflecting from *E. scolopes* were between 85 and 98% identical to each other (see FIG. 4B).

The derived amino acid sequences of the six full-length clones were aligned, demonstrating that the reflecting are highly similar (85.0-98.6%) and group into three subfamilies (FIG. 4A and B; Table 3). Analysis of their structure revealed some unusual characteristics. Reflectins possess a highly unusual amino acid composition (FIG. 4C); six amino acids (Y, M, R, N, G, D) compose over 70% of the total, and four other amino acids (A, I, L, K) are absent. Although their SDS solubility suggested that they can be membrane associated, further analyses demonstrated that they are not predicted to possess hydrophobic or charged clusters, transmembrane domains, or glycosylphosphatidylinositol anchors. However, each reflectin is composed of five repeating domains (FIG. 4). When these repeats are aligned (FIG. 3A, lower), a 'core' subdomain (SD) of 18-20 amino acids is revealed; the subdomains were defined by the presence of a repeating motif $[\alpha(X)_{4/5}MD(X)_5MD(X)_{3/4}]$. that occurs in 4 of the 5 subdomains. In this motif, X represents any amino acid; the subscripted numbers represent the number of amino acids at that position and the slash represents "or." In these subdomains 21 of 23 methionine residues occur in the same relative position in the repeat. The subdomains are enriched in M, R, G, D, S, and Q, and depleted in Y, N, W, P, and F relative to the whole protein (Table 4). Inter- and intra-protein subdomain alignments demonstrated that individual subdomains from different reflecting (e.g., SD1 from 1a vs. SD1 from 2a) are more similar to each other (80-100%) than are different subdomains (e.g., SD1 from 1a vs. SD2 from 1a) of the same reflectin (55-70%) (FIG. 4B). These data suggest greater functional constraint on the sequence within a subdomain across the family.

TABLE 4

Amino acid composition of the subdomains of reflectins and comparison to amino acid composition of the complete protein. Reflectin 1a was used as a representative protein.

| amino acid | in subdomains # | in subdomains % | outside subdomains # | outside subdomains % | in total protein # | in total protein % | depleted (−) or enriched (+) in subdomains |
|---|---|---|---|---|---|---|---|
| Y | 9  | 9.2  | 50 | 27.0 | 59 | 19.8 | − |
| M | 23 | 23.5 | 19 | 10.3 | 42 | 14.6 | + |
| R | 22 | 22.4 | 11 | 5.9  | 33 | 11.8 | + |
| N | 4  | 4.1  | 24 | 13.0 | 28 | 9.7  | − |
| G | 11 | 11.2 | 13 | 7.0  | 24 | 8.3  | + |
| D | 17 | 17.3 | 6  | 3.2  | 23 | 8.3  | + |
| W | 4  | 4.1  | 7  | 3.8  | 11 | 5.9  | − |
| S | 7  | 7.1  | 8  | 4.3  | 15 | 4.9  | + |
| P | 0  | 0.0  | 13 | 7.0  | 13 | 4.5  | − |
| Q | 10 | 10.2 | 3  | 1.6  | 13 | 4.5  | + |
| F | 2  | 2.0  | 7  | 3.8  | 9  | 2.8  | − |
| E | 0  | 0.0  | 4  | 2.2  | 4  | 1.4  | − |
| H | 0  | 0.0  | 4  | 2.2  | 4  | 1.4  | − |
| C | 0  | 0.0  | 4  | 2.2  | 4  | 1.4  | − |
| T | 0  | 0.0  | 3  | 1.6  | 3  | 0.3  | − |
| V | 0  | 0.0  | 1  | 0.5  | 1  | 0.3  | − |
| A | 0  | 0.0  | 0  | 0    | 0  | 0.0  | na |
| I | 0  | 0.0  | 0  | 0    | 0  | 0.0  | na |
| L | 0  | 0.0  | 0  | 0    | 0  | 0.0  | na |
| K | 0  | 0.0  | 0  | 0    | 0  | 0.0  | na | in subdomains, amino acid representation within all 5 subdomains (n = 98 amino acids);
outside subdomains, amino acid representation outside all 5 subdomains (n = 185 amino acids);
in total protein, representation of each amino acid in the entire sequence of the protein (n = 283 amino acids);
\#, occurrence of each amino acid;
%, percent occurrence of each amino acid;
na, not applicable.

The derived amino acid sequences of the six full-length reflectin clones were aligned, and all three tryptic peptides from reflectin protein sequencing were found in the translation of all clones (FIG. 4A underlined sequences). The alignment demonstrates that the proteins are very similar to one another as well as to the *L. forbesi* mrrp1 (FIG. 4A). Pairwise comparisons of all six sequences suggests a grouping of the *E. scolopes* reflectins into three subfamilies, reflectins 1, 2 and 3 (FIG. 4A and B), based on percentage identity of the amino acids and the positions of deletions/insertions.

As shown in FIG. 5, alignment of the polynucleotide sequences results in considerably less identity. For example, *E. scolopes* reflectins 1a, 2a, 3a, and *L. forbesi* share only 63.5% identity. Identity between the *E. scolopes* proteins is better than with *L. forbesi*, resulting in about 77.2% identity.

The *E. scolopes* reflectins have theoretical masses between 36.2 and 37.6 kDa, predicted isoelectric points between 8.80-8.84 (Table 3), and a highly unusual amino acid composition (FIG. 4C). Comparing the reflectins with other proteins by available protein analysis algorithms revealed that the reflectins possess extremely high usage of Y, M, and R, a high usage of W, and an extremely low usage of T, V, A, I, L, and K. The reflectins possess one of the highest tyrosine contents (19.8%) among current Protein Database proteins. Other tyrosine-rich proteins include an assortment of extracellular matrix and structural proteins including insect storage proteins (11-27%), keratin-associated proteins (12-17%), dental enamel peptides (13%), tyrosine-rich acidic matrix proteins (10%), and glycoproteins involved in oocyst cell wall formation in apicomplexan parasites (10%), suggesting that this amino acid may be important in the formation of protein superstructures.

Application of algorithms that predict secondary structure revealed high representation of order-promoting residues (W, Y, F, and N), the absence of 4 residues (A, I, L, and K) that are abundant in other proteins and often used in packing of hydrophobic cores, and the presence of highly ordered repeats suggest that the reflectins fold and pack in unusual ways.

Analysis of reflectin clones was carried out using MacVector 7.1.1 (Accelrys, San Diego, Calif.). Sequence alignments were performed by ClustalV. Amino acid sequence analysis was performed using the following programs available on the ExPASy Molecular Biology server (www.ExPASy.org): SignalP, PredictProtein, TMHMM, ProtParam, Radar, SAPS, nnPredict, Jpred, Sulfinator, and big-PI Predictor.

The identification and characterization of the reflectins confirmed that while the majority of animal reflective tissues are composed of purine platelets, cephalopod reflector platelets are proteinaceous. Reflectins, a previously undescribed protein family with skewed amino acid compositions, repeating domains, and localized deposition, are thus far restricted to cephalopods. They represent a striking example of natural nanofabrication of photonic structures in these animals.

Interestingly, a seventh reflectin protein sequence was identified and called reflectin 2d (SEQ ID NOs: 45 and 46) because of its homology to the other reflectin 2 proteins. Reflectin 2d was amplified from genomic DNA but has not yet been identified in the light organ cDNA pool. On an amino acid level, it is 89.7% identical to 1a, 86.4% identical to 1b, 98.9% identical to 2c, 96.0% identical to 3a and 70.5% identical to *L. forbesi* mrrp. This reflectin appears to have resulted from genomic amplification and has not yet been shown to be expressed in the LOR.

To further analyze the polypeptides and to determine the minimum functional or active portion, an RRP was prepared as described below and analyzed.

Example 5

Figure 6:
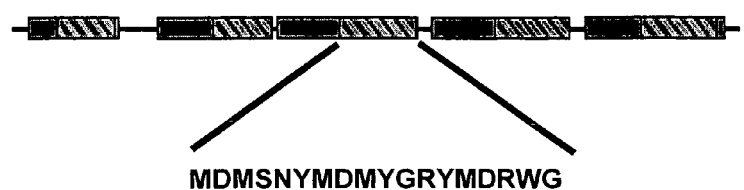
FIG. 6. Ribbon structure representing the reflectin 1A gene from *E. scolopes*. The Reflectin Repeat Peptide (RRP) amino acid sequence used herein is shown below the ribbon structure (SEQ ID NO:15).
Figure 7:
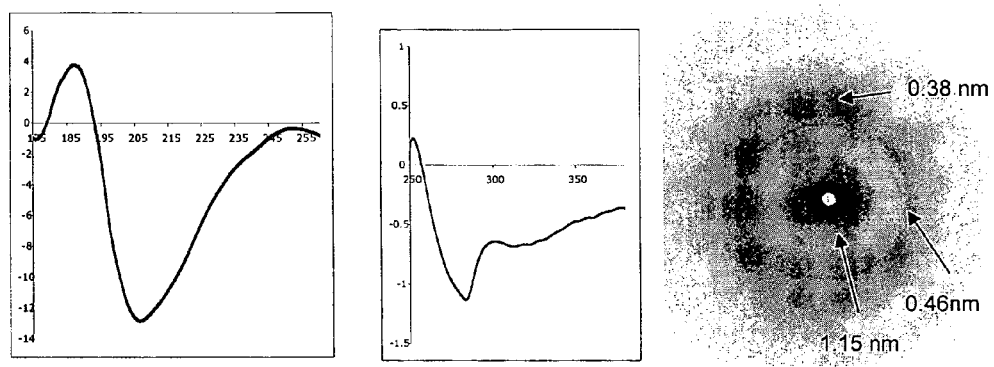
FIG. 7. (Left) Circular Dichroism of the RRP showing both near and far-UV absorbance spectra. (Right) X-ray diffraction of RRP dried in a glass capillary. The diffraction pattern is representative of beta-sheet secondary structure.

Structural Characterization of the Reflective Repeat Peptide From the Reflectin 1A Gene The 18 amino acid synthetic RRP (New England Peptide) shown in FIG. 6 (SEQ ID NO:15) was resuspended in water to a final concentration of 10 mg/ml. Secondary structure determination was undertaken using a combination of Circular Dichroism (CD) and X-ray Diffraction (FIG. 7). The CD spectrum of the suspension revealed a mostly beta-sheet character with peak absorbance at 207 nm in the far-UV. The CD spectrum of protein in the near-UV (250-350 nm) can be sensitive to certain aspects of tertiary structure. At these wavelengths the chromophores are the aromatic amino acids and disulfide bonds, and the CD signals they produce can represent a defined tertiary structure of the protein. Signals in this region are attributed to tyrosine (270-290 mn), tryptophan (280-300 nm), and disulfide bonds that give rise to a broad but weak signal throughout the near-UV spectrum. The presence of a strong near-UV signal in the CD spectrum for the RRP was an indication that the protein was folded into a well-defined orientation with a defined tertiary structure in solution. To complement the CD data, the resuspended solution was dried in a glass capillary for X-ray diffraction analysis. After drying, the protein remained optically clear and gave rise to distinct rings in the X-ray diffraction pattern at 0.38, 0.46, and 1.15 nm, indicative of a crystalline beta-sheet structure. The fact that the peptide maintained its overall secondary structure following the drying process was due to the stability of the peptide interactions.

Example 6

LVTEM Analysis

Figure 8:
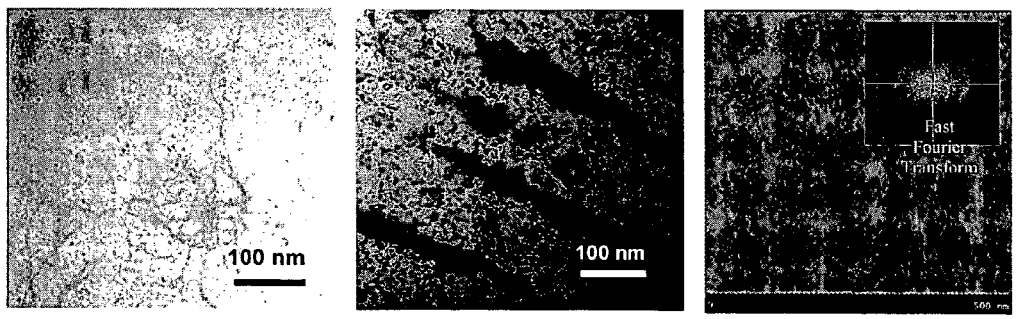
FIG. 8. (Left) LVTEM image of RRP that had recently been resuspended in water. (Middle) LVTEM image of the same RRP after it was allowed to age for approximately 6 weeks and then spotted on the TEM grid. (Right) AFM topography image and FFT of freshly resuspended RRP.

In order to determine the contribution of the peptide in higher-ordered tertiary and quaternary structures, electron microscope studies of the peptide spotted onto copper grids with an amorphous carbon support were performed. A combination of Low-voltage transmission electron microscopy (LVTEM) and High-voltage transmission electron microscopy (HVTEM) was used to characterize the peptide. Low-voltage electron microscopy allowed for imaging the protein materials without staining and prevented beam damage to otherwise delicate structures. LVTEM micrographs of newly resuspended RRP and peptide that was allowed to sit for several weeks after resuspension revealed a dramatic difference in the overall crystallinity and structure of the material. FIG. 8 shows the LVTEM images of the two samples. The newly resuspended RRP showed distinct strands and small spheres. The imaged strands were ~8 nm in diameter and the small spheres measure ~10 nm in diameter. LVTEM of the aged sample revealed a dramatically more electron dense sample and only spherical structures with diameters of ~12 nm were resolved from the image. The structure of the more electron dense regions was not resolved due to the nature of the lower electron voltage used by the microscope. Corroboration for the filamentous nature of newly resuspended RRP was obtained using Atomic Force Microscopy (AFM). The RRP was spotted onto a silicon wafer and allowed to dry in air. The AFM image showed long aligned fibrils that extended for several microns (FIG. 8). A Fast Fourier-Transformed (FFT) image of the AFM topographic image revealed that the spacing between crystals was regular and equal to 8 nm on average, revealing periodicity of the native RRP protein.

Example 7

Solubility Of Reflectins

To determine the relative solubility of reflectins, insoluble proteins were extracted from *Euprymna scolopes* light organ reflector (LOR) or eye reflectors by homogenization in 50 mM sodium phosphate buffer, pH 7.4, with 0.1 M NaCl (PBS) on ice. The total homogenate was centrifuged at 20,800×g for 15 min at 4° C. The pelleted insoluble material was then washed repeatedly in PBS. After the final wash, the material was resuspended in PBS. The resuspension was aliquotted to individual tubes. Each tube was centrifuged at 20,800×g for 15 min at 4° C. to re-pellet the insoluble material. The supernatant was discarded. The resulting pellet was resuspended in 25 µl of treatment solution and centrifuged again. The supernatant was removed, mixed with SDS-PAGE buffer, boiled for 5 min, and subjected to SDS-PAGE. Relative solubility in the presence of various reagents (Table 5) was assessed by comparison with a control sample that had been solubilized in 2% SDS.

TABLE 5

Solubility of reflectins in various reagents.

| Treatment | relative solubility of reflectins |
|---|---|
| 0.1% SDS | − |
| 0.2% SDS | ++ |
| 1–2% SDS | +++++ |
| 1% Triton X-100 | − |
| 0.5% Tween-20 | − |
| 1% CHAPS | − |
| 1M nondetergent sulfobetaine (NDSB)-195 | + |
| 1M NDSB-195 + 2% CHAPS | + |
| 1M NDSB-201 | ++ |
| 1M NDSB-201 + 2% CHAPS | + |
| 1M NDSB-256 | + |
| 1M NDSB-256 + 2% CHAPS | − |
| 1 M urea | − |
| 3 M urea | − |
| 3 M urea, 0.3 M NaCl | + |
| 8 M urea | − |
| 8 M urea, 2% CHAPS | ++ |
| 50% dimethylsulfoxide | − |
| 100% dimethylsulfoxide | ++++ |
| 100% trifluoroethanol | ++ |
| 100% acetonitrile | − |
| 0.5 M EDTA | + |
| 1 M ammonium acetate | ++ |
| 1 M ammonium sulfate | ++ |
| 1 M lithium chloride | + |
| 5 M lithium chloride | + |
| 2 M sodium chloride in PBS, pH 7.4 | + |
| 3 M sodium chloride in PBS, pH 7.4 | + |
| 0.25 M sodium sulfate, pH 6 | − |
| 0.25 M ammonium carbonate, pH 8.5 | − |
| 0.1 M sodium carbonate, pH 11 | + |

This information can be used in combination with the information gained in other Examples herein to identify the best conditions for the use, native conformation, reflectivity and solubilization of the RRP proteins.

Example 8

HVTEM Analysis

Figure 9:
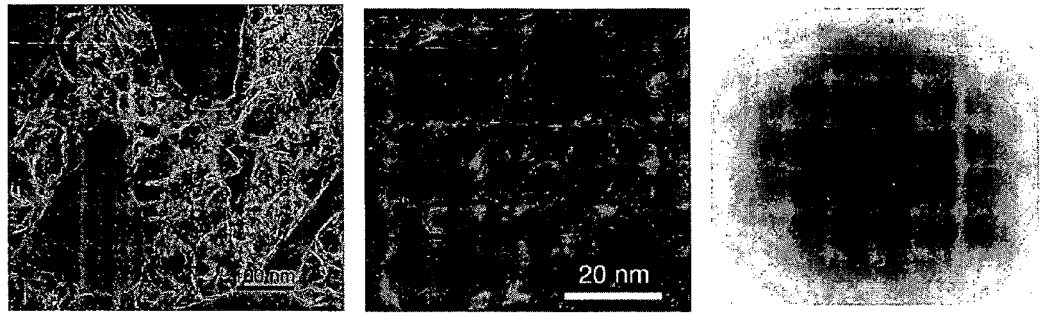
FIG. 9. (Left and Middle) HVTEM image of aged RRP showing spherical and fibril substructures at different magnifications. (Right) Electron diffraction pattern from the sample on the right. A diffraction aperture was used to limit the field as to only include the proteinaceous material.

A more detailed inspection into the molecular structure was undertaken using HVTEM. Newly resuspended RRP was largely unstable in the high-voltage beam and a high-resolution image was not obtainable. The aged peptide, with higher electron density in the LVTEM beam, was significantly more stable in the higher voltage beam and an underlying high-resolution structure was obtained. FIG. 9 shows these high-resolution images at two different magnifications. Within the RRP structure, there existed both the spherical and fibril structures noted in the LVTEM study, albeit with a tighter association between substructures. The interaction between these two structures lead to a large thread-like formation that could span between 30 and 200 nm. Due to the increased beam stability, a distinct and repeatable electron diffraction pattern was resolved and is included in FIG. 9.

Incorporation of inorganic metals to the native reflectin based platelets was theorized to provide structural stability and/or an increase in overall effective refractive index of the material. This was explored in Example 9.

Example 9

Interaction with Metals

Ultra-thin sections of the reflectin platelets are obtained. HRTEM and elemental analysis of these tissues reveals whether inorganic metals are a necessary inclusion for protein stability and contribute to the effective refractive index of the material.

Figure 10:
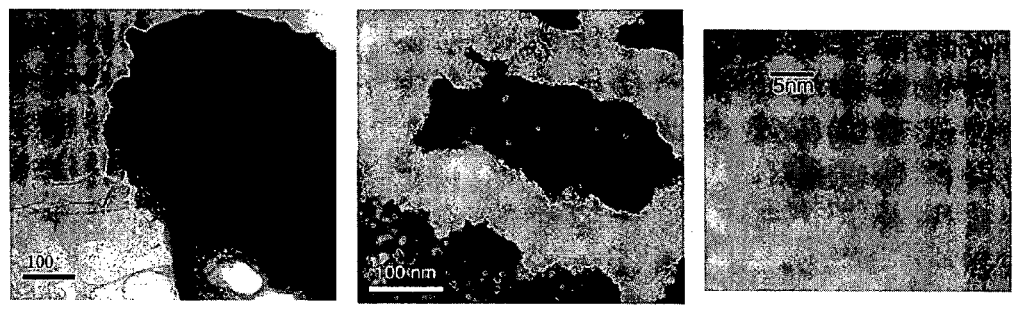
FIG. 10. (Left) LVTEM of RRP mixed with $ZnSO_4$. (Middle and Right) HVTEM of RRP mixed $AuCl_4$ at two different magnifications.

Due to the unique amino acid composition of the RRP, certain inorganic metals can be used to affect their structure and effective refractive index. 50 mM $ZnSO_4$ was added to the RRP and spotted on a copper grid for LVTEM analysis. Zn addition altered the overall structure of the RRP as seen in FIG. 10. The fibrils following Zn addition had a slightly wider diameter of ~15 mn and seemed to possess a greater rigidity. Zn is known to be important in control of both tertiary and quaternary structure of proteins and this result suggests that it plays a role in the structure of the RRP. Tyrosine residues, which are found in a high percentage of both the RRP and the full length reflectin proteins, have been demonstrated previously to potentiate the reduction of $AuCl_4$ to metallic gold with a high degree of crystallinity. Following $AuCl_4$ addition to RRP, there was an overnight precipitation of the RRP in solution. LVTEM and HVTEM images of the RRP-Au precipitate were analyzed. HRTEM images showed that the gold was able to incorporate within the microstructural framework of the RRP. Spherical gold nanoparticles were embedded within the proteinaceous material and had similar dimensions (~12 nm) of the spherical structures observed for aged RRP (FIG. 9). Composition of the nanoparticles were confirmed to be crystalline $Au^0$ by indexing the refraction pattern from these regions and measuring the lattice spacing of the nanoparticles from the high resolution image. In addition, composition of the electron-dense threads was confirmed to be a composite inorganic-organic material of RRP and Au from energy dispersive spectroscopy. The ability to incorporate inorganic metals by using the RRP as a template showed that this approach can be used to control index of refraction of the composite material and tune the material appropriately.

Figure 11:
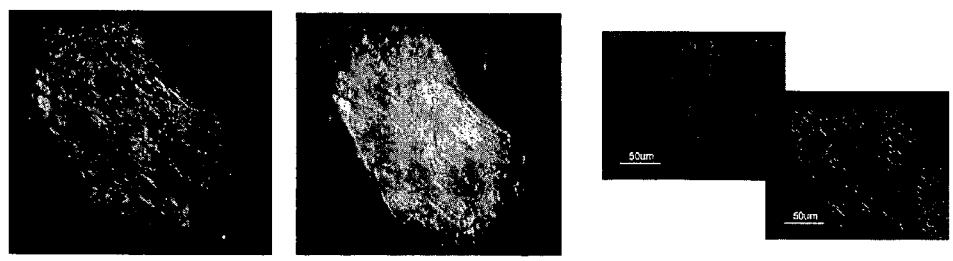
FIG. 11. (Left pair) Optical images of precipitated RRP from crystal trials at two different levels of illumination. Similar precipitation occurred in 20% of conditions tested. Images are 3 cm×3 cm. (Right pair) Optical images rotated 30° using a cross-polarized light microscope showing birefringence of the precipitated RRP shown in the left pair of images.

Bragg reflection from native platelets is hypothesized to be accomplished through the use of a high index of refraction protein material. The unique amino acid contribution of the reflectin proteins to include the aromatic residues tyrosine and tryptophan is likely to contribute to the overall bulk refractive index. The use of inorganics to increase the bulk refractive index was also discussed above. While the bulk characteristics are integral in the reflection process, it is likely that there exists a high degree of crystallinity of the protein and/or protein-inorganic matrix and is necessary in the reflection mechanism. Protein concentrations within the reflective organelles would have to be extremely high to produce the necessary refractive index mismatch with the outlying cellular components. Furthermore, if the protein bulk was generally amorphous, there would exist a high level of scatter within the reflectin organelle and reduce the overall reflectivity of the platelets. To circumvent this problem, the production of protein matrix with a high degree of crystallinity would generate a material of extremely high protein concentration with little scatter and high reflection. To determine conditions necessary for crystallization of the RRP, a number of different conditions were explored using a hanging-drop vapor diffusion protein crystallization technique. This combinatorial approach showed that in almost 20% of the conditions, the RRP precipitated out of solution within a day. Within the precipitate, the RRP appeared to possess clear regions that appeared reflective under an optical microscope with overhead illumination as seen in FIG. 11. These samples were transferred to a glass slide and viewed under a cross-polarizing microscope to determine birefringence of the material. Indeed, the material demonstrated significant birefringence as associated with ordered materials. Reversible crystallization can lead to the development of a tunable Bragg reflecting system by controlling the levels of scattered and reflected light.

The characterizations from Examples 6-9 show that the RRP sequence has the potential for mineralization/metallization of inorganics and that certain inorganics can be involved in folding (tertiary structure) of the peptide and/or the effective refractive index.

Example 10

Production of a Bacterial Expression System for Reflectin 1A

Figure 12:
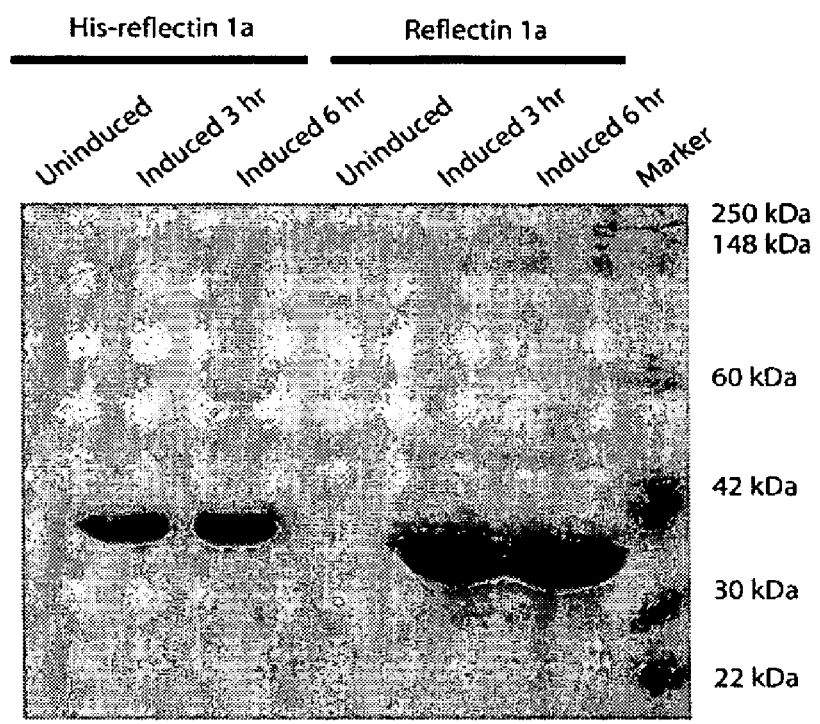
FIG. 12. Recombinant expression of the reflectin protein with (right) and without (left) the N-terminally fused HIS tag. Strong induction of the appropriately sized band on the SDS-page gel can be seen with and without the affinity tag.

In order to explore the full-length protein complex and produce large quantities of the protein, a reflectin protein that was based on the amino acid sequence from reflectin 1a was recombinantly expressed (SEQ ID NOs: 1 and 2). A synthetic gene based on this sequence was produced because of the difficulty associated with polymerase chain reaction amplification of proteins with repetitive sequences and the large arginine content of the sequence. Because of the codon bias for E. coli, DNA sequences possessing rare codons not used by this organism are not effectively recombinantly expressed. The sequence was optimized so that it best reflected the codons used natively by E. coli. Initial recombinant experiments have shown that the reflectin 1a sequence can be expressed using an IPTG induced BL21 system. SEQ ID NOS: 44 and 45 provide the nucleotide sequence of these constructs. FIG. 12 shows the expression of this sequence and one that contains a N-terminal hexa-histidine fusion to aid in subsequent purification (SEQ ID NO:45). Although in many buffers the protein is predominantly insoluble, the analyses disclosed herein permit selection of buffer components that can facilitate refolding of the recombinant protein into its native conformation.

Example 11

Use of Reflectins for Nanofabrication

Protein-based nanofabrication is a frontier area in biomimetics, in which protein structures are engineered to be used as biomaterials(Zhang, et al. *Curr. Opin. Chem. Biol.* 2002, Vol. 6, page 865, herein incorporated by reference in its entirety). For example, numerous biomaterials can be either genetically altered to produce reflectin and/or RRP proteins, including but not limited to wood, silk, cotton, flax and burlap. Alternatively, the purified reflectin and/or RRP protein can be admixed with a synthetic material to produce a semi-biomaterial, including but not limited to: polyester, metals, plastics, and the like.

Example 12

Use of Reflectins for Nanostructured Supramolecular Devices

Future embodiments of the invention provide reflectins that can support the 'bottom-up' synthesis of nanostructured supramolecular devices, especially those used in spectroscopic and optic applications (Vukusic, et al. *Nature* 2003, vol. 424, page 852, herein incorporated by reference in its entirety). For example, reflectin-based nanoreflectors can be coupled with artificial photosynthetic membranes (Steinberg-Yfach, et al., *Nature* 1997, Vol. 392, page 479, herein incorporated by reference in its entirety) or with bacteriorhodopsin-based bioelectronic devices (Wise, et al. *Trends Biotechnol.* 2002, Vol. 20, page 387, herein incorporated by reference in its entirety) to enhance the power and efficiency of these systems.

Example 13

Use as a Reporter Gene

Currently, two of the most common reporter genes for use in transcriptional studies are green fluorescent protein (GFP) and $\beta$ galactosidase. Because of their unique qualities, any of the reflectin proteins or RRPs can be used in addition to these reporter genes or as an alternative. The RRP proteins are operably linked to any promoter known to one of skill in the art that is being studied. The expression of the promoter is analyzed with respect to the amount of RRP produced as measured by spectroscopy, UV absorption, or microscopy in the presence of various filters.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be employed in various combinations by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and modifications and equivalents thereof. Accordingly, the invention is not intended to be limited by the specific disclosures of preferred embodiments herein, but instead by reference to claims attached hereto.

---

SEQUENCE LISTING

<160> NUMBER OF SEQ ID NOS: 47

<210> SEQ ID NO 1
<211> LENGTH: 852
<212> TYPE: DNA
<213> ORGANISM: Euprymna scolopes
<220> FEATURE:
<221> NAME/KEY: CDS
<222> LOCATION: (1)...(852)

<400> SEQUENCE: 1

```
atg aac cgt ttt atg aac aga tac cga ccc atg ttc aac aac atg tat        48
Met Asn Arg Phe Met Asn Arg Tyr Arg Pro Met Phe Asn Asn Met Tyr
 1               5                  10                  15 agc aac atg tac cgc ggt aga tac cga ggt atg atg gaa ccc atg tcc        96
Ser Asn Met Tyr Arg Gly Arg Tyr Arg Gly Met Met Glu Pro Met Ser
            20                  25                  30 cgt atg acc atg gac ttc caa gga aga tac atg gac tcc caa gga aga       144
Arg Met Thr Met Asp Phe Gln Gly Arg Tyr Met Asp Ser Gln Gly Arg
        35                  40                  45 atg gtc gac ccc aga tac tac gac tac tat gga aga ttc aac gac tat       192
Met Val Asp Pro Arg Tyr Tyr Asp Tyr Tyr Gly Arg Phe Asn Asp Tyr
    50                  55                  60 gac cgt tac tac gga aga tcc atg ttc aac tac ggc tgg atg atg gac       240
Asp Arg Tyr Tyr Gly Arg Ser Met Phe Asn Tyr Gly Trp Met Met Asp
 65                  70                  75                  80 ggt gat agg tac aac aga tac aac cga tgg atg gac tac ccc gag agg       288
Gly Asp Arg Tyr Asn Arg Tyr Asn Arg Trp Met Asp Tyr Pro Glu Arg
                 85                  90                  95 tac atg gac atg tct ggc tac cag atg gac atg tct gga cgc tgg atg       336
Tyr Met Asp Met Ser Gly Tyr Gln Met Asp Met Ser Gly Arg Trp Met
            100                 105                 110 gac atg cag gga cgc cac tgc aac ccg tat agc caa tgg atg atg tac       384
Asp Met Gln Gly Arg His Cys Asn Pro Tyr Ser Gln Trp Met Met Tyr
        115                 120                 125 aac tac aac aga cac ggt tac tat ccc aac tac tcc tac ggc cgc cat       432
Asn Tyr Asn Arg His Gly Tyr Tyr Pro Asn Tyr Ser Tyr Gly Arg His
    130                 135                 140 atg ttc tac ccg gag aga tgg atg gac atg tct aac tac tcc atg gac       480
Met Phe Tyr Pro Glu Arg Trp Met Asp Met Ser Asn Tyr Ser Met Asp
145                 150                 155                 160 atg tac gga cgt tac atg gac agg tgg gga cgt tac tgc aac ccg ttc       528
Met Tyr Gly Arg Tyr Met Asp Arg Trp Gly Arg Tyr Cys Asn Pro Phe
                165                 170                 175 tcc cag tac atg aat tac tat ggc aga tac tgg aac tac ccc ggg tac       576
Ser Gln Tyr Met Asn Tyr Tyr Gly Arg Tyr Trp Asn Tyr Pro Gly Tyr
            180                 185                 190 aac aac tat tat tac agc aga aac atg tac tac cca gaa aga tac ttc       624
Asn Asn Tyr Tyr Tyr Ser Arg Asn Met Tyr Tyr Pro Glu Arg Tyr Phe
        195                 200                 205 gat atg tct aac tgg cag atg gat atg cag gga cgc tgg atg gat aac       672
Asp Met Ser Asn Trp Gln Met Asp Met Gln Gly Arg Trp Met Asp Asn
    210                 215                 220 caa gga cgc tac tgc agc ccc tat tgg aac aac tgg tat ggc aga cat       720
Gln Gly Arg Tyr Cys Ser Pro Tyr Trp Asn Asn Trp Tyr Gly Arg His
```

```
Gln Gly Arg Tyr Cys Ser Pro Tyr Trp Asn Asn Trp Tyr Gly Arg His
225                 230                 235                 240 atg tac tac ccg tac cag aac aat tat ttc tac ggc cgt tat gac tat      768
Met Tyr Tyr Pro Tyr Gln Asn Asn Tyr Phe Tyr Gly Arg Tyr Asp Tyr
                    245                 250                 255 ccc gga atg gac tat tcc aac tat cag atg gac atg cag gga cgc tat      816
Pro Gly Met Asp Tyr Ser Asn Tyr Gln Met Asp Met Gln Gly Arg Tyr
                260                 265                 270 atg gac caa tac gga atg aac gac tat tac tat taa                      852
Met Asp Gln Tyr Gly Met Asn Asp Tyr Tyr Tyr *
            275                 280
```

<210> SEQ ID NO 2
<211> LENGTH: 283
<212> TYPE: PRT
<213> ORGANISM: Euprymna scolopes

<400> SEQUENCE: 2

```
Met Asn Arg Phe Met Asn Arg Tyr Arg Pro Met Phe Asn Asn Met Tyr
  1               5                  10                  15

Ser Asn Met Tyr Arg Gly Arg Tyr Arg Gly Met Met Glu Pro Met Ser
             20                  25                  30

Arg Met Thr Met Asp Phe Gln Gly Arg Tyr Met Asp Ser Gln Gly Arg
         35                  40                  45

Met Val Asp Pro Arg Tyr Tyr Asp Tyr Tyr Gly Arg Phe Asn Asp Tyr
     50                  55                  60

Asp Arg Tyr Tyr Gly Arg Ser Met Phe Asn Tyr Gly Trp Met Met Asp
 65                  70                  75                  80

Gly Asp Arg Tyr Asn Arg Tyr Asn Arg Trp Met Asp Tyr Pro Glu Arg
                 85                  90                  95

Tyr Met Asp Met Ser Gly Tyr Gln Met Asp Met Ser Gly Arg Trp Met
            100                 105                 110

Asp Met Gln Gly Arg His Cys Asn Pro Tyr Ser Gln Trp Met Met Tyr
        115                 120                 125

Asn Tyr Asn Arg His Gly Tyr Tyr Pro Asn Tyr Ser Tyr Gly Arg His
130                 135                 140

Met Phe Tyr Pro Glu Arg Trp Met Asp Met Ser Asn Tyr Ser Met Asp
145                 150                 155                 160

Met Tyr Gly Arg Tyr Met Asp Arg Trp Gly Arg Tyr Cys Asn Pro Phe
                165                 170                 175

Ser Gln Tyr Met Asn Tyr Tyr Gly Arg Tyr Trp Asn Tyr Pro Gly Tyr
            180                 185                 190

Asn Asn Tyr Tyr Tyr Ser Arg Asn Met Tyr Tyr Pro Glu Arg Tyr Phe
        195                 200                 205

Asp Met Ser Asn Trp Gln Met Asp Met Gln Gly Arg Trp Met Asp Asn
210                 215                 220

Gln Gly Arg Tyr Cys Ser Pro Tyr Trp Asn Asn Trp Tyr Gly Arg His
225                 230                 235                 240

Met Tyr Tyr Pro Tyr Gln Asn Asn Tyr Phe Tyr Gly Arg Tyr Asp Tyr
                245                 250                 255

Pro Gly Met Asp Tyr Ser Asn Tyr Gln Met Asp Met Gln Gly Arg Tyr
            260                 265                 270

Met Asp Gln Tyr Gly Met Asn Asp Tyr Tyr Tyr
        275                 280
```

<210> SEQ ID NO 3

```
<211> LENGTH: 865
<212> TYPE: DNA
<213> ORGANISM: Euprymna scolopes
<220> FEATURE:
<221> NAME/KEY: CDS
<222> LOCATION: (1)...(849)

<400> SEQUENCE: 3
```

| | | | | | | | | | | | | | | | | |
|---|---|---|---|---|---|---|---|---|---|---|---|---|---|---|---|---|
| atg | aac | cgt | ttt | atg | aac | aaa | tac | cga | ccc | atg | ttc | aac | aac | atg | tat | 48 |
| Met | Asn | Arg | Phe | Met | Asn | Lys | Tyr | Arg | Pro | Met | Phe | Asn | Asn | Met | Tyr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| agc | aac | atg | tac | cgc | ggt | aga | aac | cga | ggt | atg | atg | gag | ccc | atg | tcc | 96 |
| Ser | Asn | Met | Tyr | Arg | Gly | Arg | Asn | Arg | Gly | Met | Met | Glu | Pro | Met | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| cgt | atg | acc | atg | gac | ttc | caa | gga | aga | tac | atg | gac | tcc | cag | gga | aga | 144 |
| Arg | Met | Thr | Met | Asp | Phe | Gln | Gly | Arg | Tyr | Met | Asp | Ser | Gln | Gly | Arg | |
| | | 35 | | | | | 40 | | | | | 45 | | | | |

| | | | | | | | | | | | | | | | | |
|---|---|---|---|---|---|---|---|---|---|---|---|---|---|---|---|---|
| atg | gtc | gac | ccc | aga | tac | tac | gac | tac | tat | gga | aga | ttc | aac | gac | tat | 192 |
| Met | Val | Asp | Pro | Arg | Tyr | Tyr | Asp | Tyr | Tyr | Gly | Arg | Phe | Asn | Asp | Tyr | |
| | 50 | | | | | 55 | | | | | 60 | | | | | |

| | | | | | | | | | | | | | | | | |
|---|---|---|---|---|---|---|---|---|---|---|---|---|---|---|---|---|
| gac | cgt | tac | tac | gga | aga | tcc | atg | ttc | aac | tac | ggc | tgg | atg | atg | gac | 240 |
| Asp | Arg | Tyr | Tyr | Gly | Arg | Ser | Met | Phe | Asn | Tyr | Gly | Trp | Met | Met | Asp | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ggt | gat | agg | tac | aac | aga | tac | aac | cga | tgg | atg | gac | tac | ccc | gag | agg | 288 |
| Gly | Asp | Arg | Tyr | Asn | Arg | Tyr | Asn | Arg | Trp | Met | Asp | Tyr | Pro | Glu | Arg | |
| | | | | 85 | | | | | 90 | | | | | 95 | | |

| | | | | | | | | | | | | | | | | |
|---|---|---|---|---|---|---|---|---|---|---|---|---|---|---|---|---|
| tac | atg | gac | atg | tct | ggc | tat | cag | atg | gac | atg | tct | gga | cgc | tgg | atg | 336 |
| Tyr | Met | Asp | Met | Ser | Gly | Tyr | Gln | Met | Asp | Met | Ser | Gly | Arg | Trp | Met | |
| | | | 100 | | | | | 105 | | | | | 110 | | | |

| | | | | | | | | | | | | | | | | |
|---|---|---|---|---|---|---|---|---|---|---|---|---|---|---|---|---|
| gac | atg | cag | gga | cgc | cac | tgc | aac | ccg | tac | agc | cag | tgg | ggt | tac | aac | 384 |
| Asp | Met | Gln | Gly | Arg | His | Cys | Asn | Pro | Tyr | Ser | Gln | Trp | Gly | Tyr | Asn | |
| | | 115 | | | | | 120 | | | | | 125 | | | | |

| | | | | | | | | | | | | | | | | |
|---|---|---|---|---|---|---|---|---|---|---|---|---|---|---|---|---|
| tat | aat | aga | cac | ggt | tac | tat | ccc | aac | tac | tcc | tac | ggc | cgt | cat | atg | 432 |
| Tyr | Asn | Arg | His | Gly | Tyr | Tyr | Pro | Asn | Tyr | Ser | Tyr | Gly | Arg | His | Met | |
| | 130 | | | | | 135 | | | | | 140 | | | | | |

| | | | | | | | | | | | | | | | | |
|---|---|---|---|---|---|---|---|---|---|---|---|---|---|---|---|---|
| ttc | tac | cca | gaa | aga | tgg | atg | gac | atg | tct | ggt | tat | cag | atg | gat | atg | 480 |
| Phe | Tyr | Pro | Glu | Arg | Trp | Met | Asp | Met | Ser | Gly | Tyr | Gln | Met | Asp | Met | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| caa | ggt | cgc | tat | atg | gac | aga | tgg | ggc | cgt | tat | tgc | aac | ccg | ttc | tcc | 528 |
| Gln | Gly | Arg | Tyr | Met | Asp | Arg | Trp | Gly | Arg | Tyr | Cys | Asn | Pro | Phe | Ser | |
| | | | | 165 | | | | | 170 | | | | | 175 | | |

| | | | | | | | | | | | | | | | | |
|---|---|---|---|---|---|---|---|---|---|---|---|---|---|---|---|---|
| cag | tac | atg | aat | tat | tat | ggc | aga | tac | tgg | aac | tac | ccc | gga | tat | aac | 576 |
| Gln | Tyr | Met | Asn | Tyr | Tyr | Gly | Arg | Tyr | Trp | Asn | Tyr | Pro | Gly | Tyr | Asn | |
| | | | 180 | | | | | 185 | | | | | 190 | | | |

| | | | | | | | | | | | | | | | | |
|---|---|---|---|---|---|---|---|---|---|---|---|---|---|---|---|---|
| agc | tat | tat | aac | agc | agg | aat | atg | ttc | tac | cca | gaa | aga | tac | ttc | gat | 624 |
| Ser | Tyr | Tyr | Asn | Ser | Arg | Asn | Met | Phe | Tyr | Pro | Glu | Arg | Tyr | Phe | Asp | |
| | | 195 | | | | | 200 | | | | | 205 | | | | |

| | | | | | | | | | | | | | | | | |
|---|---|---|---|---|---|---|---|---|---|---|---|---|---|---|---|---|
| atg | tct | aac | tgg | cag | atg | gat | atg | cag | gga | cgc | tgg | atg | gat | aac | caa | 672 |
| Met | Ser | Asn | Trp | Gln | Met | Asp | Met | Gln | Gly | Arg | Trp | Met | Asp | Asn | Gln | |
| | 210 | | | | | 215 | | | | | 220 | | | | | |

| | | | | | | | | | | | | | | | | |
|---|---|---|---|---|---|---|---|---|---|---|---|---|---|---|---|---|
| gga | cgt | tac | tgt | agc | cct | tat | tgg | aac | aac | tgg | tat | ggc | aga | cag | atg | 720 |
| Gly | Arg | Tyr | Cys | Ser | Pro | Tyr | Trp | Asn | Asn | Trp | Tyr | Gly | Arg | Gln | Met | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tac | tac | ccg | tac | cag | aac | aat | tat | ttc | tat | ggc | cgt | tat | gac | tat | ccc | 768 |
| Tyr | Tyr | Pro | Tyr | Gln | Asn | Asn | Tyr | Phe | Tyr | Gly | Arg | Tyr | Asp | Tyr | Pro | |
| | | | | 245 | | | | | 250 | | | | | 255 | | |

| | | | | | | | | | | | | | | | | |
|---|---|---|---|---|---|---|---|---|---|---|---|---|---|---|---|---|
| gga | atg | gac | tat | tcc | aac | tat | cag | atg | gac | atg | cag | gga | cgc | tat | atg | 816 |
| Gly | Met | Asp | Tyr | Ser | Asn | Tyr | Gln | Met | Asp | Met | Gln | Gly | Arg | Tyr | Met | |
| | | | 260 | | | | | 265 | | | | | 270 | | | |

| | | | | | | | | | |
|---|---|---|---|---|---|---|---|---|---|
| gac | caa | tac | gga | atg | aac | gac | tat | tgc | tat | taa atattaaata gtttag | 865 |
| Asp | Gln | Tyr | Gly | Met | Asn | Asp | Tyr | Cys | Tyr | * | |

<210> SEQ ID NO 4
<211> LENGTH: 282
<212> TYPE: PRT
<213> ORGANISM: Euprymna scolopes

<400> SEQUENCE: 4

```
Met Asn Arg Phe Met Asn Lys Tyr Arg Pro Met Phe Asn Asn Met Tyr
1               5                   10                  15

Ser Asn Met Tyr Arg Gly Arg Asn Arg Gly Met Met Glu Pro Met Ser
            20                  25                  30

Arg Met Thr Met Asp Phe Gln Gly Arg Tyr Met Asp Ser Gln Gly Arg
        35                  40                  45

Met Val Asp Pro Arg Tyr Tyr Asp Tyr Tyr Gly Arg Phe Asn Asp Tyr
50                  55                  60

Asp Arg Tyr Tyr Gly Arg Ser Met Phe Asn Tyr Gly Trp Met Met Asp
65                  70                  75                  80

Gly Asp Arg Tyr Asn Arg Tyr Asn Arg Trp Met Asp Tyr Pro Glu Arg
                85                  90                  95

Tyr Met Asp Met Ser Gly Tyr Gln Met Asp Met Ser Gly Arg Trp Met
            100                 105                 110

Asp Met Gln Gly Arg His Cys Asn Pro Tyr Ser Gln Trp Gly Tyr Asn
        115                 120                 125

Tyr Asn Arg His Gly Tyr Tyr Pro Asn Tyr Ser Tyr Gly Arg His Met
    130                 135                 140

Phe Tyr Pro Glu Arg Trp Met Asp Met Ser Gly Tyr Gln Met Asp Met
145                 150                 155                 160

Gln Gly Arg Tyr Met Asp Arg Trp Gly Arg Tyr Cys Asn Pro Phe Ser
                165                 170                 175

Gln Tyr Met Asn Tyr Tyr Gly Arg Tyr Trp Asn Tyr Pro Gly Tyr Asn
            180                 185                 190

Ser Tyr Tyr Asn Ser Arg Asn Met Phe Tyr Pro Glu Arg Tyr Phe Asp
        195                 200                 205

Met Ser Asn Trp Gln Met Asp Met Gln Gly Arg Trp Met Asp Asn Gln
    210                 215                 220

Gly Arg Tyr Cys Ser Pro Tyr Trp Asn Trp Tyr Gly Arg Gln Met
225                 230                 235                 240

Tyr Tyr Pro Tyr Gln Asn Asn Tyr Phe Tyr Gly Arg Tyr Asp Tyr Pro
                245                 250                 255

Gly Met Asp Tyr Ser Asn Tyr Gln Met Asp Met Gln Gly Arg Tyr Met
            260                 265                 270

Asp Gln Tyr Gly Met Asn Asp Tyr Cys Tyr
        275                 280
```

<210> SEQ ID NO 5
<211> LENGTH: 852
<212> TYPE: DNA
<213> ORGANISM: Euprymna scolopes
<220> FEATURE:
<221> NAME/KEY: CDS
<222> LOCATION: (1)...(852)

<400> SEQUENCE: 5

```
atg aac cgt tac atg acc cga ttc cgt aac ttc tac ggc aac atg tac     48
Met Asn Arg Tyr Met Thr Arg Phe Arg Asn Phe Tyr Gly Asn Met Tyr
1               5                   10                  15
```

```
cgc ggt aga tac cga gga atg atg gaa ccc atg tcc cgt atg acc atg      96
Arg Gly Arg Tyr Arg Gly Met Met Glu Pro Met Ser Arg Met Thr Met
         20                  25                  30 gac ttc caa gga aga tac atg gac tcc cag gga aga atg gtc gac ccc     144
Asp Phe Gln Gly Arg Tyr Met Asp Ser Gln Gly Arg Met Val Asp Pro
 35                  40                  45 aga tac tac gac tac tat gga aga tac aac gac tat gac cgt tac tac     192
Arg Tyr Tyr Asp Tyr Tyr Gly Arg Tyr Asn Asp Tyr Asp Arg Tyr Tyr
     50                  55                  60 gga aga tcc atg ttc aac tac ggt tgg atg atg gac ggt gat agg tac     240
Gly Arg Ser Met Phe Asn Tyr Gly Trp Met Met Asp Gly Asp Arg Tyr
 65                  70                  75                  80 aac aga tac aac cga tgg atg gac ttc ccc gag agg tac atg gac atg     288
Asn Arg Tyr Asn Arg Trp Met Asp Phe Pro Glu Arg Tyr Met Asp Met
                 85                  90                  95 tct ggc tac cag atg gac atg tac gga cgc tgg atg gac atg cag gga     336
Ser Gly Tyr Gln Met Asp Met Tyr Gly Arg Trp Met Asp Met Gln Gly
             100                 105                 110 cgc cac tgc aac ccg tat agc caa tgg atg atg tac aac tac aac aga     384
Arg His Cys Asn Pro Tyr Ser Gln Trp Met Met Tyr Asn Tyr Asn Arg
         115                 120                 125 cac ggt tac tat ccc aac tac tcc tac ggc cgc cat atg ttc tac ccg     432
His Gly Tyr Tyr Pro Asn Tyr Ser Tyr Gly Arg His Met Phe Tyr Pro
     130                 135                 140 gag aga tgg atg gac atg tct aac tac tcc atg gac atg tac gga cgt     480
Glu Arg Trp Met Asp Met Ser Asn Tyr Ser Met Asp Met Tyr Gly Arg
145                 150                 155                 160 tac atg gac agg tgg gga cgt tac tgc aac ccg ttc tac caa ttc tac     528
Tyr Met Asp Arg Trp Gly Arg Tyr Cys Asn Pro Phe Tyr Gln Phe Tyr
                 165                 170                 175 aac cac tgg aac cgc tac ggc aac tac ccc ggg tac tat aac tac tac     576
Asn His Trp Asn Arg Tyr Gly Asn Tyr Pro Gly Tyr Tyr Asn Tyr Tyr
             180                 185                 190 tac atg tac tac ccg gaa aga tat ttc gac atg tct aac tgg cag atg     624
Tyr Met Tyr Tyr Pro Glu Arg Tyr Phe Asp Met Ser Asn Trp Gln Met
         195                 200                 205 gat atg cag gga cgc tgg atg gat atg cag gga cgc tac tgc agc ccc     672
Asp Met Gln Gly Arg Trp Met Asp Met Gln Gly Arg Tyr Cys Ser Pro
     210                 215                 220 tat tgg tac aac tgg tat ggc aga cat atg tac tac ccc tac cag aac     720
Tyr Trp Tyr Asn Trp Tyr Gly Arg His Met Tyr Tyr Pro Tyr Gln Asn
225                 230                 235                 240 tac tat tgg tac ggc cgt tat gac tat ccc ggg atg gac tat tcc aac     768
Tyr Tyr Trp Tyr Gly Arg Tyr Asp Tyr Pro Gly Met Asp Tyr Ser Asn
                 245                 250                 255 tgg cag atg gat atg cag gga cgc tgg atg gat atg caa ggg cga tac     816
Trp Gln Met Asp Met Gln Gly Arg Trp Met Asp Met Gln Gly Arg Tyr
             260                 265                 270 atg gat tat ccc tat aat tat tac aac tgg tat taa                     852
Met Asp Tyr Pro Tyr Asn Tyr Tyr Asn Trp Tyr *
         275                 280

<210> SEQ ID NO 6
<211> LENGTH: 283
<212> TYPE: PRT
<213> ORGANISM: Euprymna scolopes

<400> SEQUENCE: 6

Met Asn Arg Tyr Met Thr Arg Phe Arg Asn Phe Tyr Gly Asn Met Tyr
 1               5                   10                  15
```

```
Arg Gly Arg Tyr Arg Gly Met Met Glu Pro Met Ser Arg Met Thr Met
            20                  25                  30

Asp Phe Gln Gly Arg Tyr Met Asp Ser Gln Gly Arg Met Val Asp Pro
        35                  40                  45

Arg Tyr Tyr Asp Tyr Tyr Gly Arg Tyr Asn Asp Tyr Asp Arg Tyr Tyr
    50                  55                  60

Gly Arg Ser Met Phe Asn Tyr Gly Trp Met Met Asp Gly Asp Arg Tyr
65                  70                  75                  80

Asn Arg Tyr Asn Arg Trp Met Asp Phe Pro Glu Arg Tyr Met Asp Met
                85                  90                  95

Ser Gly Tyr Gln Met Asp Met Tyr Gly Arg Trp Met Asp Met Gln Gly
            100                 105                 110

Arg His Cys Asn Pro Tyr Ser Gln Trp Met Met Tyr Asn Tyr Asn Arg
        115                 120                 125

His Gly Tyr Tyr Pro Asn Tyr Ser Tyr Gly Arg His Met Phe Tyr Pro
    130                 135                 140

Glu Arg Trp Met Asp Met Ser Asn Tyr Ser Met Asp Met Tyr Gly Arg
145                 150                 155                 160

Tyr Met Asp Arg Trp Gly Arg Tyr Cys Asn Pro Phe Tyr Gln Phe Tyr
                165                 170                 175

Asn His Trp Asn Arg Tyr Gly Asn Tyr Pro Gly Tyr Tyr Asn Tyr Tyr
            180                 185                 190

Tyr Met Tyr Tyr Pro Glu Arg Tyr Phe Asp Met Ser Asn Trp Gln Met
        195                 200                 205

Asp Met Gln Gly Arg Trp Met Asp Met Gln Gly Arg Tyr Cys Ser Pro
    210                 215                 220

Tyr Trp Tyr Asn Trp Tyr Gly Arg His Met Tyr Tyr Pro Tyr Gln Asn
225                 230                 235                 240

Tyr Tyr Trp Tyr Gly Arg Tyr Asp T

-continued

```
Gly Arg Ser Met Phe Asn Tyr Gly Trp Met Met Asp Gly Asp Arg Tyr
 65                  70                  75                  80 aac aga tgc aac cga tgg atg gac tac ccc gag agg tac atg gac atg    288
Asn Arg Cys Asn Arg Trp Met Asp Tyr Pro Glu Arg Tyr Met Asp Met
                 85                  90                  95 tct ggc tat cag atg gac atg tac gga cgc tgg atg gac atg cag gga    336
Ser Gly Tyr Gln Met Asp Met Tyr Gly Arg Trp Met Asp Met Gln Gly
            100                 105                 110 cgc cac tgc aac ccg tat agc caa tgg atg atg tac aac tac aac aga    384
Arg His Cys Asn Pro Tyr Ser Gln Trp Met Met Tyr Asn Tyr Asn Arg
        115                 120                 125 cac ggt tac tat ccc aac tac tcc tac ggc cgc cat atg ttc tac ccg    432
His Gly Tyr Tyr Pro Asn Tyr Ser Tyr Gly Arg His Met Phe Tyr Pro
    130                 135                 140 gag aga tgg atg gac atg tct aac tac tcc atg gac atg tac gga cgt    480
Glu Arg Trp Met Asp Met Ser Asn Tyr Ser Met Asp Met Tyr Gly Arg
145                 150                 155                 160 tac atg gac agg tgg gga cgt tac tgc aac ccg ttc tac caa ttc tac    528
Tyr Met Asp Arg Trp Gly Arg Tyr Cys Asn Pro Phe Tyr Gln Phe Tyr
                165                 170                 175 aac cac tgg aac cgc tac ggc aac tac ccc ggg tac tat aac tac tac    576
Asn His Trp Asn Arg Tyr Gly Asn Tyr Pro Gly Tyr Tyr Asn Tyr Tyr
            180                 185                 190 tac atg tac tac ccg gaa aga tat ttc ggc atg tct aac tgg cag atg    624
Tyr Met Tyr Tyr Pro Glu Arg Tyr Phe Gly Met Ser Asn Trp Gln Met
        195                 200                 205 gat atg cag gga cgc tgg atg gat atg cag gga cgc tac tgc agc ccc    672
Asp Met Gln Gly Arg Trp Met Asp Met Gln Gly Arg Tyr Cys Ser Pro
    210                 215                 220 tat tgg tac aac tgg tat ggc aga cat atg tac tac ccc tac cag aac    720
Tyr Trp Tyr Asn Trp Tyr Gly Arg His Met Tyr Tyr Pro Tyr Gln Asn
225                 230                 235                 240 tac tat tgg tac ggc cgt tat gac tat ccc ggg atg gac tat tcc aac    768
Tyr Tyr Trp Tyr Gly Arg Tyr Asp Tyr Pro Gly Met Asp Tyr Ser Asn
                245                 250                 255 tgg cag atg gat atg cag gga cgc tgg atg gac atg caa ggg cga tac    816
Trp Gln Met Asp Met Gln Gly Arg Trp Met Asp Met Gln Gly Arg Tyr
            260                 265                 270 atg gat tat ccc tat aat tat tac aac tgg aat cac tag                855
Met Asp Tyr Pro Tyr Asn Tyr Tyr Asn Trp Asn His *
        275                 280

<210> SEQ ID NO 8
<211> LENGTH: 284
<212> TYPE: PRT
<213> ORGANISM: Euprymna scolopes

<400> SEQUENCE: 8

Met Asn Arg Tyr Met Asn Arg Phe Arg Asn Phe Tyr Gly Asn Met Tyr
 1               5                  10                  15

Arg Gly Arg Tyr Arg Gly Met Met Glu Pro Met Ser Arg Met Thr Met
            20                  25                  30

Asp Phe Gln Gly Arg Tyr Met Asp Ser Gln Gly Arg Met Val Asp Pro
        35                  40                  45

Arg Phe Tyr Asp Tyr Tyr Gly Arg Tyr Asn Asp Tyr Asp Arg Tyr Tyr
    50                  55                  60

Gly Arg Ser Met Phe Asn Tyr Gly Trp Met Met Asp Gly Asp Arg Tyr
 65                  70                  75                  80

Asn Arg Cys Asn Arg Trp Met Asp Tyr Pro Glu Arg Tyr Met Asp Met
```

```
                        85                  90                  95
Ser Gly Tyr Gln Met Asp Met Tyr Gly Arg Trp Met Asp Met Gln Gly
                100                 105                 110

Arg His Cys Asn Pro Tyr Ser Gln Trp Met Met Tyr Asn Tyr Asn Arg
            115                 120                 125

His Gly Tyr Tyr Pro Asn Tyr Ser Tyr Gly Arg His Met Phe Tyr Pro
        130                 135                 140

Glu Arg Trp Met Asp Met Ser Asn Tyr Ser Met Asp Met Tyr Gly Arg
145                 150                 155                 160

Tyr Met Asp Arg Trp Gly Arg Tyr Cys Asn Pro Phe Tyr Gln Phe Tyr
                165                 170                 175

Asn His Trp Asn Arg Tyr Gly Asn Tyr Pro Gly Tyr Tyr Asn Tyr Tyr
            180                 185                 190

Tyr Met Tyr Tyr Pro Glu Arg Tyr Phe Gly Met Ser Asn Trp Gln Met
        195                 200                 205

Asp Met Gln Gly Arg Trp Met Asp Met Gln Gly Arg Tyr Cys Ser Pro
    210                 215                 220

Tyr Trp Tyr Asn Trp Tyr Gly Arg His Met Tyr Tyr Pro Tyr Gln Asn
225                 230                 235                 240

Tyr Tyr Trp Tyr Gly Arg Tyr Asp Tyr Pro Gly Met Asp Tyr Ser Asn
                245                 250                 255

Trp Gln Met Asp Met Gln Gly Arg Trp Met Asp Met Gln Gly Arg Tyr
            260                 265                 270

Met Asp Tyr Pro Tyr Asn Tyr Tyr Asn Trp Asn His
        275                 280

<210> SEQ ID NO 9
<211> LENGTH: 897
<212> TYPE: DNA
<213> ORGANISM: Euprymna scolopes
<220> FEATURE:
<221> NAME/KEY: CDS
<222> LOCATION: (1)...(894)

<400> SEQUENCE: 9 atg aat cgt tac atg aac cga ttc cgt aac ttc tac ggc aac atg tac      48
Met Asn Arg Tyr Met Asn Arg Phe Arg Asn Phe Tyr Gly Asn Met Tyr
1               5                   10                  15 cgc ggt aga tac cga ggg atg atg gaa ccc atg tct cgt atg acc atg      96
Arg Gly Arg Tyr Arg Gly Met Met Glu Pro Met Ser Arg Met Thr Met
            20                  25                  30 gac ttc caa gga aga tac atg gac tct cag gga aga atg gtc gac cct     144
Asp Phe Gln Gly Arg Tyr Met Asp Ser Gln Gly Arg Met Val Asp Pro
        35                  40                  45 aga tac tac gac tac tat gga aga tac aac gac tat gac cgt tac tac     192
Arg Tyr Tyr Asp Tyr Tyr Gly Arg Tyr Asn Asp Tyr Asp Arg Tyr Tyr
    50                  55                  60 gga aga tcc atg ttc aac tac ggc tgg atg atg gac ggt gat agg tac     240
Gly Arg Ser Met Phe Asn Tyr Gly Trp Met Met Asp Gly Asp Arg Tyr
65                  70                  75                  80 aac aga tac aac cga tgg atg gac ttc ccc gag agg tac atg gac atg     288
Asn Arg Tyr Asn Arg Trp Met Asp Phe Pro Glu Arg Tyr Met Asp Met
                85                  90                  95 tct ggc tac cag atg gac atg tac gga cgc tgg atg gac atg cag gga     336
Ser Gly Tyr Gln Met Asp Met Tyr Gly Arg Trp Met Asp Met Gln Gly
            100                 105                 110 cgc cac tgc aac ccg tat agc caa tgg atg atg tac aac tac aac aga     384
Arg His Cys Asn Pro Tyr Ser Gln Trp Met Met Tyr Asn Tyr Asn Arg
```

```
                    115                 120                 125
cac ggt tac tat ccc aac tac tcc tac ggc cgc cat atg ttc tac ccg       432
His Gly Tyr Tyr Pro Asn Tyr Ser Tyr Gly Arg His Met Phe Tyr Pro
    130                 135                 140 gag aga tgg atg gac atg tct aac tac tcc atg gac atg tac gga cgt       480
Glu Arg Trp Met Asp Met Ser Asn Tyr Ser Met Asp Met Tyr Gly Arg
145                 150                 155                 160 tac atg gac agg tgg gga cgt tac tgc aac ccg ttc tac caa ttc tac       528
Tyr Met Asp Arg Trp Gly Arg Tyr Cys Asn Pro Phe Tyr Gln Phe Tyr
                165                 170                 175 aac cac tgg aac cgc tac ggc aac tac ccc ggg tac tat aac tac tac       576
Asn His Trp Asn Arg Tyr Gly Asn Tyr Pro Gly Tyr Tyr Asn Tyr Tyr
            180                 185                 190 tac atg tac tac ccg gaa aga tat ttc gac atg tct aac tgg cag atg       624
Tyr Met Tyr Tyr Pro Glu Arg Tyr Phe Asp Met Ser Asn Trp Gln Met
        195                 200                 205 gat atg cag gga cgc tgg atg gat atg cag gga cgc tac tgc agc cct       672
Asp Met Gln Gly Arg Trp Met Asp Met Gln Gly Arg Tyr Cys Ser Pro
    210                 215                 220 tat tgg tac aac tgg tat ggc aga cag atg tac tac ccc tac cag aac       720
Tyr Trp Tyr Asn Trp Tyr Gly Arg Gln Met Tyr Tyr Pro Tyr Gln Asn
225                 230                 235                 240 tac tat tgg tac ggc cgt tat gac tat ccc gga atg gac tat tcc aac       768
Tyr Tyr Trp Tyr Gly Arg Tyr Asp Tyr Pro Gly Met Asp Tyr Ser Asn
                245                 250                 255 tac ggc cgt tat gac tat ccc gga atg gac tat tcc aac tat cag atg       816
Tyr Gly Arg Tyr Asp Tyr Pro Gly Met Asp Tyr Ser Asn Tyr Gln Met
            260                 265                 270 gat atg cag gga cga tat atg gac atg caa ggg cga tac atg gat tat       864
Asp Met Gln Gly Arg Tyr Met Asp Met Gln Gly Arg Tyr Met Asp Tyr
        275                 280                 285 ccc tat aat tat tac aac tgg aat cac tag tga                           897
Pro Tyr Asn Tyr Tyr Asn Trp Asn His *
    290                 295

<210> SEQ ID NO 10
<211> LENGTH: 297
<212> TYPE: PRT
<213> ORGANISM: Euprymna scolopes

<400> SEQUENCE: 10

Met Asn Arg Tyr Met Asn Arg Phe Arg Asn Phe Tyr Gly Asn Met Tyr
1               5                   10                  15

Arg Gly Arg Tyr Arg Gly Met Met Glu Pro Met Ser Arg Met Thr Met
                20                  25                  30

Asp Phe Gln Gly Arg Tyr Met Asp Ser Gln Gly Arg Met Val Asp Pro
            35                  40                  45

Arg Tyr Tyr Asp Tyr Tyr Gly Arg Tyr Asn Asp Tyr Asp Arg Tyr Tyr
        50                  55                  60

Gly Arg Ser Met Phe Asn Tyr Gly Trp Met Met Asp Gly Asp Arg Tyr
65              70                  75                  80

Asn Arg Tyr Asn Arg Trp Met Asp Phe Pro Glu Arg Tyr Met Asp Met
                85                  90                  95

Ser Gly Tyr Gln Met Asp Met Tyr Gly Arg Trp Met Asp Met Gln Gly
            100                 105                 110

Arg His Cys Asn Pro Tyr Ser Gln Trp Met Met Tyr Asn Tyr Asn Arg
        115                 120                 125

His Gly Tyr Tyr Pro Asn Tyr Ser Tyr Gly Arg His Met Phe Tyr Pro
```

```
                130                 135                 140
Glu Arg Trp Met Asp Met Ser Asn Tyr Ser Met Asp Met Tyr Gly Arg
145                 150                 155                 160

Tyr Met Asp Arg Trp Gly Arg Tyr Cys Asn Pro Phe Tyr Gln Phe Tyr
                165                 170                 175

Asn His Trp Asn Arg Tyr Gly Asn Tyr Pro Gly Tyr Tyr Asn Tyr Tyr
            180                 185                 190

Tyr Met Tyr Tyr Pro Glu Arg Tyr Phe Asp Met Ser Asn Trp Gln Met
        195                 200                 205

Asp Met Gln Gly Arg Trp Met Asp Met Gln Gly Arg Tyr Cys Ser Pro
    210                 215                 220

Tyr Trp Tyr Asn Trp Tyr Gly Arg Gln Met Tyr Tyr Pro Tyr Gln Asn
225                 230                 235                 240

Tyr Tyr Trp Tyr Gly Arg Tyr Asp Tyr Pro Gly Met Asp Tyr Ser Asn
                245                 250                 255

Tyr Gly Arg Tyr Asp Tyr Pro Gly Met Asp Tyr Ser Asn Tyr Gln Met
            260                 265                 270

Asp Met Gln Gly Arg Tyr Met Asp Met Gln Gly Arg Tyr Met Asp Tyr
        275                 280                 285

Pro Tyr Asn Tyr Tyr Asn Trp Asn His
    290                 295

<210> SEQ ID NO 11
<211> LENGTH: 867
<212> TYPE: DNA
<213> ORGANISM: Euprymna scolopes
<220> FEATURE:
<221> NAME/KEY: CDS
<222> LOCATION: (1)...(867)

<400> SEQUENCE: 11 atg aac cgt tac atg aac cga ttc cgt aac ttt tac ggc aac atg tgc        48
Met Asn Arg Tyr Met Asn Arg Phe Arg Asn Phe Tyr Gly Asn Met Cys
  1               5                  10                  15 cgc aac aga aac cgc ggt atg atg gag ccg atg tcc cgt atg acc atg        96
Arg Asn Arg Asn Arg Gly Met Met Glu Pro Met Ser Arg Met Thr Met
             20                  25                  30 gac ttc caa gga aga tac atg gac tcc cag gga aga atg gtc gac ccc       144
Asp Phe Gln Gly Arg Tyr Met Asp Ser Gln Gly Arg Met Val Asp Pro
         35                  40                  45 agg tac tac gac tac tat gga aga tac aac gac tac gac cgt tat tac       192
Arg Tyr Tyr Asp Tyr Tyr Gly Arg Tyr Asn Asp Tyr Asp Arg Tyr Tyr
     50                  55                  60 gga aga tcc atg ttc aat tac ggc tgg atg atg gac ggt gat agg tac       240
Gly Arg Ser Met Phe Asn Tyr Gly Trp Met Met Asp Gly Asp Arg Tyr
 65                  70                  75                  80 aac aga tac aac cga tgg atg gac tac cca gag agg tac atg gac atg       288
Asn Arg Tyr Asn Arg Trp Met Asp Tyr Pro Glu Arg Tyr Met Asp Met
                 85                  90                  95 tct ggc tac cag atg gac atg tac gga cgc tgg atg gac atg cag gga       336
Ser Gly Tyr Gln Met Asp Met Tyr Gly Arg Trp Met Asp Met Gln Gly
            100                 105                 110 cgc cac tgc aac ccg tac agc caa tgg atg atg tac aac tac aac aga       384
Arg His Cys Asn Pro Tyr Ser Gln Trp Met Met Tyr Asn Tyr Asn Arg
        115                 120                 125 cac ggt tac tat ccc aac tac tcc tac ggc cgt cat atg ttc tac ccg       432
His Gly Tyr Tyr Pro Asn Tyr Ser Tyr Gly Arg His Met Phe Tyr Pro
    130                 135                 140
```

```
gag aga tgg atg gac atg tct aac tac tcc atg gac atg tac gga cgt    480
Glu Arg Trp Met Asp Met Ser Asn Tyr Ser Met Asp Met Tyr Gly Arg
145                 150                 155                 160 tac atg gac agg tgg gga cgt tac tgc aac ccg ttc tat cac tat tac    528
Tyr Met Asp Arg Trp Gly Arg Tyr Cys Asn Pro Phe Tyr His Tyr Tyr
            165                 170                 175 aac cac tgg aac cgc tcc ggc aac aac ccc ggg tac tat agc tac tac    576
Asn His Trp Asn Arg Ser Gly Asn Asn Pro Gly Tyr Tyr Ser Tyr Tyr
        180                 185                 190 tac atg tac tac cca gag aga tac ttc gac atg tct aac tgg cag atg    624
Tyr Met Tyr Tyr Pro Glu Arg Tyr Phe Asp Met Ser Asn Trp Gln Met
    195                 200                 205 gat atg cag gga cgc tgg atg gat atg cag gga cgc tac tgc agc ccc    672
Asp Met Gln Gly Arg Trp Met Asp Met Gln Gly Arg Tyr Cys Ser Pro
210                 215                 220 tat tgg tac aac tgg tat ggc aga cag atg tac tac ccc tac cag aac    720
Tyr Trp Tyr Asn Trp Tyr Gly Arg Gln Met Tyr Tyr Pro Tyr Gln Asn
225                 230                 235                 240 tac tat tgg tac ggc cga tgg gac tat ccc gga atg gac tat tcc aac    768
Tyr Tyr Trp Tyr Gly Arg Trp Asp Tyr Pro Gly Met Asp Tyr Ser Asn
            245                 250                 255 tgg cag atg gat atg cag gga cgc tgg atg gac atg cag gga cga tac    816
Trp Gln Met Asp Met Gln Gly Arg Trp Met Asp Met Gln Gly Arg Tyr
        260                 265                 270 atg gac ccc tgg tgg atg aac gac tcc tac tac aat aac tac tac aat    864
Met Asp Pro Trp Trp Met Asn Asp Ser Tyr Tyr Asn Asn Tyr Tyr Asn
    275                 280                 285 taa                                                                867
*

<210> SEQ ID NO 12
<211> LENGTH: 288
<212> TYPE: PRT
<213> ORGANISM: Euprymna scolopes

<400> SEQUENCE: 12

Met Asn Arg Tyr Met Asn Arg Phe Arg Asn Phe Tyr Gly Asn Met Cys
1               5                   10                  15

Arg Asn Arg Asn Arg Gly Met Met Glu Pro Met Ser Arg Met Thr Met
            20                  25                  30

Asp Phe Gln Gly Arg Tyr Met Asp Ser Gln Gly Arg Met Val Asp Pro
        35                  40                  45

Arg Tyr Tyr Asp Tyr Tyr Gly Arg Tyr Asn Asp Tyr Asp Arg Tyr Tyr
    50                  55                  60

Gly Arg Ser Met Phe Asn Tyr Gly Trp Met Met Asp Gly Asp Arg Tyr
65                  70                  75                  80

Asn Arg Tyr Asn Arg Trp Met Asp Tyr Pro Glu Arg Tyr Met Asp Met
                85                  90                  95

Ser Gly Tyr Gln Met Asp Met Tyr Gly Arg Trp Met Asp Met Gln Gly
            100                 105                 110

Arg His Cys Asn Pro Tyr Ser Gln Trp Met Met Tyr Asn Tyr Asn Arg
        115                 120                 125

His Gly Tyr Tyr Pro Asn Tyr Ser Tyr Gly Arg His Met Phe Tyr Pro
    130                 135                 140

Glu Arg Trp Met Asp Met Ser Asn Tyr Ser Met Asp Met Tyr Gly Arg
145                 150                 155                 160

Tyr Met Asp Arg Trp Gly Arg Tyr Cys Asn Pro Phe Tyr His Tyr Tyr
                165                 170                 175
```

```
Asn His Trp Asn Arg Ser Gly Asn Asn Pro Gly Tyr Tyr Ser Tyr Tyr
            180                 185                 190

Tyr Met Tyr Tyr Pro Glu Arg Tyr Phe Asp Met Ser Asn Trp Gln Met
        195                 200                 205

Asp Met Gln Gly Arg Trp Met Asp Met Gln Gly Arg Tyr Cys Ser Pro
    210                 215                 220

Tyr Trp Tyr Asn Trp Tyr Gly Arg Gln Met Tyr Tyr Pro Tyr Gln Asn
225                 230                 235                 240

Tyr Tyr Trp Tyr Gly Arg Trp Asp Tyr Pro Gly Met Asp Tyr Ser Asn
                245                 250                 255

Trp Gln Met Asp Met Gln Gly Arg Trp Met Asp Met Gln Gly Arg Tyr
            260                 265                 270

Met Asp Pro Trp Trp Met Asn Asp Ser Tyr Tyr Asn Asn Tyr Tyr Asn
        275                 280                 285
```

<210> SEQ ID NO 13
<211> LENGTH: 1301
<212> TYPE: DNA
<213> ORGANISM: Loligo forbesi
<220> FEATURE:
<221> NAME/KEY: CDS
<222> LOCATION: (99)...(893)
<220> FEATURE:
<221> NAME/KEY: misc_feature
<222> LOCATION: 1163
<223> OTHER INFORMATION: n = A,T,C or G

<400> SEQUENCE: 13

```
gagaactcca gctgttcctt acttgtttgt cgtcttctga cagaagtcca acgtctttcc      60
aatcttcttc agcaactaca gctgtatacg aaatcatc atg aac cgc tct atg aac    116
                                          Met Asn Arg Ser Met Asn
                                            1               5 aga tac caa ccc agc aac atg tgg ggc aat atg aac aga gat aga tac      164
Arg Tyr Gln Pro Ser Asn Met Trp Gly Asn Met Asn Arg Asp Arg Tyr
            10                  15                  20 agt ggt atg atg gaa ccc atg tcc aga atg agc atg gac ttc caa gga      212
Ser Gly Met Met Glu Pro Met Ser Arg Met Ser Met Asp Phe Gln Gly
        25                  30                  35 aga cac atg gac tcc atg gac aga atg gtc gac ccc gga aga tgg aac      260
Arg His Met Asp Ser Met Asp Arg Met Val Asp Pro Gly Arg Trp Asn
    40                  45                  50 gac tat gac cgt tac tac gga agg tcc acg ttt aat tat ggc tgg atg      308
Asp Tyr Asp Arg Tyr Tyr Gly Arg Ser Thr Phe Asn Tyr Gly Trp Met
55                  60                  65                  70 gag aac ggt gac aga ttc aac agg aac ctc cgc cct atg gac ttc ccc      356
Glu Asn Gly Asp Arg Phe Asn Arg Asn Leu Arg Pro Met Asp Phe Pro
                75                  80                  85 gag agg tac atg gac atg tct gac tat cag atg gac atg ggc gga cgc      404
Glu Arg Tyr Met Asp Met Ser Asp Tyr Gln Met Asp Met Gly Gly Arg
            90                  95                  100 tgg atg gac cca tac gga cgc cag tgc aac cca ttc aac cag tgt ggt      452
Trp Met Asp Pro Tyr Gly Arg Gln Cys Asn Pro Phe Asn Gln Cys Gly
        105                 110                 115 tac aac aga cat ggt tac tat cct ggc tac tcc tac ggt cgt aac atg      500
Tyr Asn Arg His Gly Tyr Tyr Pro Gly Tyr Ser Tyr Gly Arg Asn Met
    120                 125                 130 tgt tac ccc gag aga tgg atg gac atg tct aac tac tcc atg gat atg      548
Cys Tyr Pro Glu Arg Trp Met Asp Met Ser Asn Tyr Ser Met Asp Met
135                 140                 145                 150
```

```
cag gga cgc tac atg gac aga cgg ggt cgt cat tgc aac ccg ttc tct      596
Gln Gly Arg Tyr Met Asp Arg Arg Gly Arg His Cys Asn Pro Phe Ser
                155                 160                 165 cag cac acg aat tgg tac ggt aga tat cgg aat tat ccc ggt gat aat      644
Gln His Thr Asn Trp Tyr Gly Arg Tyr Arg Asn Tyr Pro Gly Asp Asn
            170                 175                 180 aac tac tac aac aga aac atg tac tat ccc gag aga cat ttt gat atg      692
Asn Tyr Tyr Asn Arg Asn Met Tyr Tyr Pro Glu Arg His Phe Asp Met
        185                 190                 195 tcc aac tgg cag atg gat atg cag gga cgc tgg atg gat aat cag gga      740
Ser Asn Trp Gln Met Asp Met Gln Gly Arg Trp Met Asp Asn Gln Gly
    200                 205                 210 cgc tac aac aac ccc tac tgg tac gga aga aac atg tac cag ccc tac      788
Arg Tyr Asn Asn Pro Tyr Trp Tyr Gly Arg Asn Met Tyr Gln Pro Tyr
215                 220                 225                 230 cag aat aat cag tgg tcc ggc cga tgg gac tat ccc gga atg gac tgc      836
Gln Asn Asn Gln Trp Ser Gly Arg Trp Asp Tyr Pro Gly Met Asp Cys
                235                 240                 245 ggt atg gac atg cag gga ggt tac atg aat aat agt aat gaa ggg gac      884
Gly Met Asp Met Gln Gly Gly Tyr Met Asn Asn Ser Asn Glu Gly Asp
            250                 255                 260 tat cta tag ccttctttag ggggagattt acattttttt ttaattaaaa              933
Tyr Leu * aatgtctatc ttttttaacg aaatttcgag tttattcat tgtataaaat ccattgaagt      993
ttaatggaaa acgtttaatc agaatatatg gagagaatgg aaaaatggag aaagaattat   1053
ccaaaatggc tgccaataaa ttcggaatgg cttcaagcaa gactaaaaga aatggttaaa   1113
gcagacgaga gatcaaaaca tcattccatt ttcttatttg aatagggcn ccaagaaaga    1173 aaactgaagc gcgaaaagac tgaaatttaa tcttttttttt ttaaatcaat gaatttttat  1233
atgatttatt gtaatattac gaaataaaac tatatatttt cgttctaaaa aaaaaaaaa    1293 aaaaaaaa                                                            1301

<210> SEQ ID NO 14
<211> LENGTH: 264
<212> TYPE: PRT
<213> ORGANISM: Loligo forbesi

<400> SEQUENCE: 14

Met Asn Arg Ser Met Asn Arg Tyr Gln Pro Ser Asn Met Trp Gly Asn
1               5                   10                  15

Met Asn Arg Asp Arg Tyr Ser Gly Met Met Glu Pro Met Ser Arg Met
            20                  25                  30

Ser Met Asp Phe Gln Gly Arg His Met Asp Ser Met Asp Arg Met Val
        35                  40                  45

Asp Pro Gly Arg Trp Asn Asp Tyr Asp Arg Tyr Tyr Gly Arg Ser Thr
    50                  55                  60

Phe Asn Tyr Gly Trp Met Glu Asn Gly Asp Arg Phe Asn Arg Asn Leu
65                  70                  75                  80

Arg Pro Met Asp Phe Pro Glu Arg Tyr Met Asp Met Ser Asp Tyr Gln
                85                  90                  95

Met Asp Met Gly Gly Arg Trp Met Asp Pro Tyr Gly Arg Gln Cys Asn
            100                 105                 110

Pro Phe Asn Gln Cys Gly Tyr Asn Arg His Gly Tyr Tyr Pro Gly Tyr
        115                 120                 125

Ser Tyr Gly Arg Asn Met Cys Tyr Pro Glu Arg Trp Met Asp Met Ser
    130                 135                 140
```

```
Asn Tyr Ser Met Asp Met Gln Gly Arg Tyr Met Asp Arg Arg Gly Arg
145                 150                 155                 160

His Cys Asn Pro Phe Ser Gln His Thr Asn Trp Tyr Gly Arg Tyr Arg
                165                 170                 175

Asn Tyr Pro Gly Asp Asn Asn Tyr Tyr Asn Arg Asn Met Tyr Tyr Pro
            180                 185                 190

Glu Arg His Phe Asp Met Ser Asn Trp Gln Met Asp Met Gln Gly Arg
            195                 200                 205

Trp Met Asp Asn Gln Gly Arg Tyr Asn Asn Pro Tyr Trp Tyr Gly Arg
        210                 215                 220

Asn Met Tyr Gln Pro Tyr Gln Asn Asn Gln Trp Ser Gly Arg Trp Asp
225                 230                 235                 240

Tyr Pro Gly Met Asp Cys Gly Met Asp Met Gln Gly Tyr Met Asn
                245                 250                 255

Asn Ser Asn Glu Gly Asp Tyr Leu
            260
```

```
<210> SEQ ID NO 15
<211> LENGTH: 18
<212> TYPE: PRT
<213> ORGANISM: Artificial Sequence
<220> FEATURE:
<223> OTHER INFORMATION: Reflectin Repeat peptide RRP

<400> SEQUENCE: 15

Met Asp Met Ser Asn Tyr Met Asp Met Tyr Gly Arg Tyr Met Asp Arg
1               5                   10                  15

Trp Gly
```

```
<210> SEQ ID NO 16
<211> LENGTH: 18
<212> TYPE: PRT
<213> ORGANISM: Artificial Sequence
<220> FEATURE:
<223> OTHER INFORMATION: Reflectin Repeat region SD1.

<400> SEQUENCE: 16

Met Ser Arg Met Thr Met Asp Phe Gln Gly Arg Tyr Met Asp Ser Gln
1               5                   10                  15

Gly Arg
```

```
<210> SEQ ID NO 17
<211> LENGTH: 20
<212> TYPE: PRT
<213> ORGANISM: Artificial Sequence
<220> FEATURE:
<223> OTHER INFORMATION: Reflectin Repeat region SD2.

<400> SEQUENCE: 17

Met Asp Met Ser Gly Tyr Gln Met Asp Met Ser Gly Arg Trp Met Asp
1               5                   10                  15

Met Gln Gly Arg
            20
```

```
<210> SEQ ID NO 18
<211> LENGTH: 20
<212> TYPE: PRT
<213> ORGANISM: Artificial Sequence
<220> FEATURE:
<223> OTHER INFORMATION: Reflectin Repeat region SD3.
```

-continued

```
<400> SEQUENCE: 18

Met Asp Met Ser Asn Tyr Ser Met Asp Met Tyr Gly Arg Tyr Met Asp
 1               5                  10                  15

Arg Trp Gly Arg
            20

<210> SEQ ID NO 19
<211> LENGTH: 20
<212> TYPE: PRT
<213> ORGANISM: Artificial Sequence
<220> FEATURE:
<223> OTHER INFORMATION: Reflectin Repeat region SD3.

<400> SEQUENCE: 19

Met Asp Met Ser Gly Tyr Gln Met Asp Met Gln Gly Arg Tyr Met Asp
 1               5                  10                  15

Arg Trp Gly Arg
            20

<210> SEQ ID NO 20
<211> LENGTH: 20
<212> TYPE: PRT
<213> ORGANISM: Artificial Sequence
<220> FEATURE:
<223> OTHER INFORMATION: Reflectin Repeat region SD4.

<400> SEQUENCE: 20

Phe Asp Met Ser Asn Trp Gln Met Asp Met Gln Gly Arg Trp Met Asp
 1               5                  10                  15

Asn Gln Gly Arg
            20

<210> SEQ ID NO 21
<211> LENGTH: 20
<212> TYPE: PRT
<213> ORGANISM: Artificial Sequence
<220> FEATURE:
<223> OTHER INFORMATION: Reflectin Repeat region SD4.

<400> SEQUENCE: 21

Phe Gly Met Ser Asn Trp Gln Met Asp Met Gln Gly Arg Trp Met Asp
 1               5                  10                  15

Asn Gln Gly Arg
            20

<210> SEQ ID NO 22
<211> LENGTH: 18
<212> TYPE: PRT
<213> ORGANISM: Artificial Sequence
<220> FEATURE:
<223> OTHER INFORMATION: Reflectin Repeat region SD5.

<400> SEQUENCE: 22

Met Asp Tyr Ser Asn Tyr Gln Met Asp Met Gln Gly Arg Tyr Met Asp
 1               5                  10                  15

Tyr Gly

<210> SEQ ID NO 23
<211> LENGTH: 20
<212> TYPE: PRT
<213> ORGANISM: Artificial Sequence
<220> FEATURE:
<223> OTHER INFORMATION: Reflectin Repeat region SD5.
```

-continued

```
<400> SEQUENCE: 23

Met Asp Tyr Ser Asn Trp Gln Met Asp Met Gln Gly Arg Trp Met Asp
 1               5                  10                  15

Met Gln Gly Arg
            20

<210> SEQ ID NO 24
<211> LENGTH: 20
<212> TYPE: PRT
<213> ORGANISM: Artificial Sequence
<220> FEATURE:
<223> OTHER INFORMATION: Reflectin Repeat region SD5.

<400> SEQUENCE: 24

Met Asp Tyr Ser Asn Tyr Gln Met Asp Met Gln Gly Arg Tyr Met Asp
 1               5                  10                  15

Met Gln Gly Arg
            20

<210> SEQ ID NO 25
<211> LENGTH: 19
<212> TYPE: PRT
<213> ORGANISM: Artificial Sequence
<220> FEATURE:
<223> OTHER INFORMATION: Reflectin Repeat Peptide.

<400> SEQUENCE: 25

Phe Asp Met Ser Asn Trp Gln Met Asp Met Gln Gly Arg Tyr Met Asp
 1               5                  10                  15

Gln Tyr Gly

<210> SEQ ID NO 26
<211> LENGTH: 20
<212> TYPE: PRT
<213> ORGANISM: Artificial Sequence
<220> FEATURE:
<223> OTHER INFORMATION: Prophetic Reflectin peptide.

<400> SEQUENCE: 26

Met Asp Met Ser Asn Tyr Ser Met Asp Met Gln Gly Arg Trp Met Asp
 1               5                  10                  15

Asn Gln Gly Arg
            20

<210> SEQ ID NO 27
<211> LENGTH: 20
<212> TYPE: PRT
<213> ORGANISM: Artificial Sequence
<220> FEATURE:
<223> OTHER INFORMATION: Prophetic Reflectin peptide.

<400> SEQUENCE: 27

Met Asp Met Ser Gly Tyr Gln Met Asp Met Gly Gly Arg Trp Met Asp
 1               5                  10                  15

Met Gln Gly Arg
            20

<210> SEQ ID NO 28
<211> LENGTH: 18
<212> TYPE: PRT
<213> ORGANISM: Artificial Sequence
<220> FEATURE:
<223> OTHER INFORMATION: Prophetic Reflectin peptide.
```

-continued

```
<400> SEQUENCE: 28

Met Ser Arg Met Thr Met Asp Phe Gln Gly Arg Tyr Met Asp Arg Trp
1               5                   10                  15

Gly Arg

<210> SEQ ID NO 29
<211> LENGTH: 20
<212> TYPE: PRT
<213> ORGANISM: Artificial Sequence
<220> FEATURE:
<223> OTHER INFORMATION: Prophetic Reflectin peptide.

<400> SEQUENCE: 29

Phe Asp Met Ser Asn Trp Gln Met Asp Met Gln Gly Arg Tyr Met Asp
1               5                   10                  15

Gln Tyr Gly Arg
            20

<210> SEQ ID NO 30
<211> LENGTH: 20
<212> TYPE: PRT
<213> ORGANISM: Artificial Sequence
<220> FEATURE:
<223> OTHER INFORMATION: Prophetic Reflectin peptide.

<400> SEQUENCE: 30

Phe Asp Met Ser Arg Met Thr Met Asp Phe Gln Gly Arg Tyr Met Asp
1               5                   10                  15

Ser Gln Gly Arg
            20

<210> SEQ ID NO 31
<211> LENGTH: 13
<212> TYPE: PRT
<213> ORGANISM: Artificial Sequence
<220> FEATURE:
<223> OTHER INFORMATION: Tryptic Reflectin peptide.

<400> SEQUENCE: 31

Ser Met Phe Asn Tyr Gly Trp Met Met Asp Gly Asp Arg
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Tryptic Reflectin peptide.

<400> SEQUENCE: 32

Glu Gly Tyr Tyr Pro Asn Tyr Ser Tyr Gly Arg
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Tryptic Reflectin peptide.

<400> SEQUENCE: 33

Tyr Phe Asp Met Ser Asn Trp Gln Met Asp Met Gln Gly Arg
1               5                   10
```

<210> SEQ ID NO 34
<211> LENGTH: 27
<212> TYPE: DNA
<213> ORGANISM: Artificial Sequence
<220> FEATURE:
<223> OTHER INFORMATION: Synthetic Oligonucleotide Primer Sequence 33F3

<400> SEQUENCE: 34
cgccactgca acccgtatag ccaatgg                                27

<210> SEQ ID NO 35
<211> LENGTH: 24
<212> TYPE: DNA
<213> ORGANISM: Artificial Sequence
<220> FEATURE:
<223> OTHER INFORMATION: Synthetic Oligonucleotide Primer Sequence 33R2

<400> SEQUENCE: 35
ccaatagggg ctgcagtagc gtcc                                   24

<210> SEQ ID NO 36
<211> LENGTH: 28
<212> TYPE: DNA
<213> ORGANISM: Artificial Sequence
<220> FEATURE:
<223> OTHER INFORMATION: Synthetic Oligonucleotide Primer Sequence 33R3

<400> SEQUENCE: 36
gttgccggag cggttccagt ggttgtaa                               28

<210> SEQ ID NO 37
<211> LENGTH: 26
<212> TYPE: DNA
<213> ORGANISM: Artificial Sequence
<220> FEATURE:
<223> OTHER INFORMATION: Synthetic Oligonucleotide Primer Sequence 33R4

<400> SEQUENCE: 37
cccggggtag ttccagtatc tgccat                                 26

<210> SEQ ID NO 38
<211> LENGTH: 26
<212> TYPE: DNA
<213> ORGANISM: Artificial Sequence
<220> FEATURE:
<223> OTHER INFORMATION: Synthetic Oligonucleotide Primer Sequence 33AF

<400> SEQUENCE: 38
atgaaccgtt ttatgaacag ataccg                                 26

<210> SEQ ID NO 39
<211> LENGTH: 26
<212> TYPE: DNA
<213> ORGANISM: Artificial Sequence
<220> FEATURE:
<223> OTHER INFORMATION: Synthetic Oligonucleotide Primer Sequence 33BF

<400> SEQUENCE: 39
atgaaccgtt acatgaaccg attccg                                 26

<210> SEQ ID NO 40
<211> LENGTH: 28
<212> TYPE: DNA
<213> ORGANISM: Artificial Sequence
<220> FEATURE:
<223> OTHER INFORMATION: Synthetic Oligonucleotide Primer Sequence 33A1R -continued
<210> SEQ ID NO 41
<211> LENGTH: 27
<212> TYPE: DNA
<213> ORGANISM: Artificial Sequence
<220> FEATURE:
<223> OTHER INFORMATION: Synthetic Oligonucleotide Primer Sequence 33B1R

<400> SEQUENCE: 41
gagcaagacg ttcaagaatt tcagacg                                    27

<210> SEQ ID NO 42
<211> LENGTH: 28
<212> TYPE: DNA
<213> ORGANISM: Artificial Sequence
<220> FEATURE:
<223> OTHER INFORMATION: Synthetic Oligonucleotide Primer Sequence 33B2R

<400> SEQUENCE: 42
ccagttgtaa taattatagg gataatcc                                   28

<210> SEQ ID NO 43
<211> LENGTH: 27
<212> TYPE: DNA
<213> ORGANISM: Artificial Sequence
<220> FEATURE:
<223> OTHER INFORMATION: Synthetic Oligonucleotide Primer Sequence 33BR

<400> SEQUENCE: 43
ccatgtatcg tccctgcatg tccatcc                                    27

<210> SEQ ID NO 44
<211> LENGTH: 912
<212> TYPE: DNA
<213> ORGANISM: Artificial Sequence
<220> FEATURE:
<223> OTHER INFORMATION: E. coli codon usage for Reflectin 1a.

<400> SEQUENCE: 44 cat atg gga tcc atg aac cgc ttt atg aat cgt tat cgc ccg atg ttt      48 aac aat atg tat agc aac atg tat cgc ggc cgt tat cgc ggt atg atg      96 gaa ccg atg tcg cgc atg acc atg gat ttc cag ggc cgt tac atg gat     144 agc cag ggg cgc atg gtg gac ccg cgc tat tac gac tat tac ttt aac     192 gac tac gat cgt tat tac ggc cgt agc atg ttc aac tat ggt tgg atg     240 atg gat ggc gat cgc tat aat cgt tat aat cgc tgg atg gac tat cca     288 gaa cgc tat atg gat atg agc ggt tac cag atg gat atg tcg ggc cgt     336 tgg atg gac atg caa ggt cgc cat tgt aac ccg tat tcc cag tgg atg     384 atg tat aac tac aat cgt cat ggt tac tat cca aac tac tct tat ggc     432 cgc cac atg ttt tac ccg gag cgt tgg atg gat atg agt aac tat agc     480 atg gat atg tac ggt cgc tac atg gat cgc tgg ggt cgt tac tgc aat     528 ccg ttc tcg cag tat atg aac tac tac ggc cgc tat tgg aat tac ccg     576 ggt tat aac aat tat tat tac agc cgc aac atg tat tac ccg gaa cgt     624 tac ttt gat atg agc aac tgg cag atg gac atg cag ggc cgt tgg atg     672 gat aat cag ggg cgc tat tgc tcc ccg tat tgg aat aac tac ggt cgc     720

-continued

```
cac atg tat tac cca tac caa aac aac tat ccg ttt tac ggc cgt tat        768 gac tac ccg ggc atg gat tat agc aat tac caa atg gat cag ggg cgc        816 tat atg gat cag tac ggt atg aac gat tat tac tat taa tgtacaagat         865 ccagatctaa gcttggtacc acgcgtgcgc gctgattcgg ctgctaa                    912
```

<210> SEQ ID NO 45
<211> LENGTH: 859
<212> TYPE: DNA
<213> ORGANISM: Euprymna scolopes
<220> FEATURE:
<221> NAME/KEY: CDS
<222> LOCATION: (1)...(855)

<400> SEQUENCE: 45

```
atg aac cgt tac atg aac cga ttc cgt aac ttc tac ggc aac atg tac         48
Met Asn Arg Tyr Met Asn Arg Phe Arg Asn Phe Tyr Gly Asn Met Tyr
 1               5                  10                  15 cgc ggt aga tac cga gga atg atg gaa ccc atg tcc cgt atg acc atg         96
Arg Gly Arg Tyr Arg Gly Met Met Glu Pro Met Ser Arg Met Thr Met
            20                  25                  30 gac ttc caa gga aga tac atg gac tcc cag gga aga atg gtc gac ccc        144
Asp Phe Gln Gly Arg Tyr Met Asp Ser Gln Gly Arg Met Val Asp Pro
        35                  40                  45 aga tac tac gac tac tat gga cga ttc aac gac tat gac cgt tac tac        192
Arg Tyr Tyr Asp Tyr Tyr Gly Arg Phe Asn Asp Tyr Asp Arg Tyr Tyr
    50                  55                  60 gga aga tcc atg ttc aat tac ggc tgg atg atg gac ggt gat agg tac        240
Gly Arg Ser Met Phe Asn Tyr Gly Trp Met Met Asp Gly Asp Arg Tyr
65                  70                  75                  80 aac aga tac aac cga tgg atg gac ttc ccc gag agg tat atg gac atg        288
Asn Arg Tyr Asn Arg Trp Met Asp Phe Pro Glu Arg Tyr Met Asp Met
                85                  90                  95 tct ggc tac cag atg gac atg tac gga cgc tgg atg gac atg cag gga        336
Ser Gly Tyr Gln Met Asp Met Tyr Gly Arg Trp Met Asp Met Gln Gly
            100                 105                 110 cgc cac tgc aac ccg tac agc caa tgg atg atg tac aac tac aac aga        384
Arg His Cys Asn Pro Tyr Ser Gln Trp Met Met Tyr Asn Tyr Asn Arg
        115                 120                 125 cac ggt tac tat ccc aac tac tcc tac ggc cgc cat atg ttc tac ccg        432
His Gly Tyr Tyr Pro Asn Tyr Ser Tyr Gly Arg His Met Phe Tyr Pro
    130                 135                 140 gag aga tgg atg gac atg tct aac tac tcc atg gac atg tac gga cgt        480
Glu Arg Trp Met Asp Met Ser Asn Tyr Ser Met Asp Met Tyr Gly Arg
145                 150                 155                 160 tac atg gac agg tgg gga cgt tac tgc aac ccg ttc tac caa ttc tac        528
Tyr Met Asp Arg Trp Gly Arg Tyr Cys Asn Pro Phe Tyr Gln Phe Tyr
                165                 170                 175 aac cac tgg aac cgc tac ggc aac tac ccc ggg tac tat agc tac tac        576
Asn His Trp Asn Arg Tyr Gly Asn Tyr Pro Gly Tyr Tyr Ser Tyr Tyr
            180                 185                 190 tac atg tac tac cca gag aga tac ttc gac atg tct aac tgg cag atg        624
Tyr Met Tyr Tyr Pro Glu Arg Tyr Phe Asp Met Ser Asn Trp Gln Met
        195                 200                 205 gat atg cag gga cgc tgg atg gat atg cag gga cgc tac tgc agc ccc        672
Asp Met Gln Gly Arg Trp Met Asp Met Gln Gly Arg Tyr Cys Ser Pro
    210                 215                 220 tat tgg tac aat tgg tat ggc aga cat atg tac tac ccc tac cag aac        720
Tyr Trp Tyr Asn Trp Tyr Gly Arg His Met Tyr Tyr Pro Tyr Gln Asn
225                 230                 235                 240
```

```
tac tat tgg tac ggc cgt tat gac tat ccc ggg atg gac tat tcc aac         768
Tyr Tyr Trp Tyr Gly Arg Tyr Asp Tyr Pro Gly Met Asp Tyr Ser Asn
            245                 250                 255 tgg cag atg gat atg cag gga cgc tgg atg gat atg caa ggg cga tac         816
Trp Gln Met Asp Met Gln Gly Arg Trp Met Asp Met Gln Gly Arg Tyr
        260                 265                 270 atg gat tat ccc tat aat tat tac aac tgg aat cac tag gtga               859
Met Asp Tyr Pro Tyr Asn Tyr Tyr Asn Trp Asn His *
    275                 280

<210> SEQ ID NO 46
<211> LENGTH: 284
<212> TYPE: PRT
<213> ORGANISM: Euprymna scolopes

<400> SEQUENCE: 46

Met Asn Arg Tyr Met Asn Arg Phe Arg Asn Phe Tyr Gly Asn Met Tyr
 1               5                  10                  15

Arg Gly Arg Tyr Arg Gly Met Met Glu Pro Met Ser Arg Met Thr Met
            20                  25                  30

Asp Phe Gln Gly Arg Tyr Met Asp Ser Gln Gly Arg Met Val Asp Pro
        35                  40                  45

Arg Tyr Tyr Asp Tyr Tyr Gly Arg Phe Asn Asp Tyr Asp Arg Tyr Tyr
    50                  55                  60

Gly Arg Ser Met Phe Asn Tyr Gly Trp Met Met Asp Gly Asp Arg Tyr
65                  70                  75                  80

Asn Arg Tyr Asn Arg Trp Met Asp Phe Pro Glu Arg Tyr Met Asp Met
                85                  90                  95

Ser Gly Tyr Gln Met Asp Met Tyr Gly Arg Trp Met Asp Met Gln Gly
            100                 105                 110

Arg His Cys Asn Pro Tyr Ser Gln Trp Met Met Tyr Asn Tyr Asn Arg
        115                 120                 125

His Gly Tyr Tyr Pro Asn Tyr Ser Tyr Gly Arg His Met Phe Tyr Pro
    130                 135                 140

Glu Arg Trp Met Asp Met Ser Asn Tyr Ser Asp Met Tyr Gly Arg
145                 150                 155                 160

Tyr Met Asp Arg Trp Gly Arg Tyr Cys Asn Pro Phe Tyr Gln Phe Tyr
                165                 170                 175

Asn His Trp Asn Arg Tyr Gly Asn Tyr Pro Gly Tyr Tyr Ser Tyr Tyr
            180                 185                 190

Tyr Met Tyr Tyr Pro Glu Arg Tyr Phe Asp Met Ser Asn Trp Gln Met
        195                 200                 205

Asp Met Gln Gly Arg Trp Met Asp Met Gln Gly Arg Tyr Cys Ser Pro
    210                 215                 220

Tyr Trp Tyr Asn Trp Tyr Gly Arg His Met Tyr Tyr Pro Tyr Gln Asn
225                 230                 235                 240

Tyr Tyr Trp Tyr Gly Arg Tyr Asp Tyr Pro Gly Met Asp Tyr Ser Asn
                245                 250                 255

Trp Gln Met Asp Met Gln Gly Arg Trp Met Asp Met Gln Gly Arg Tyr
            260                 265                 270

Met Asp Tyr Pro Tyr Asn Tyr Tyr Asn Trp Asn His
        275                 280

<210> SEQ ID NO 47
<211> LENGTH: 19
<212> TYPE: PRT
```

```
-continued
<213> ORGANISM: Artificial Sequence
<220> FEATURE:
<223> OTHER INFORMATION: Reflectin Repeat peptide.

<400> SEQUENCE: 47

Met Asp Tyr Ser Asn Tyr Gln Met Asp Met Gln Gly Arg Tyr Met Asp
 1               5                  10                  15

Gln Gly Arg
```

What is claimed is:

1. A biomimetic reflective material comprising a first component, the first component comprising at least one polypeptide selected from the group consisting of:
   (a) a reflectin polypeptide having at least 87.2% identity to SEQ ID NO:2;
   (b) a polypeptide having at least one and not more than four repeat units of the reflectin polypeptide;
   (c) a polypeptide comprising at least six repeat units of the reflectin polypeptide; and
   (d) any combination of (a) through (c); the first component being in combination with at least a second component compatible with the first component, such that the combination forms a biomimetic reflective material.

2. The biomimetic reflective material of claim 1, the material comprising a metal ion.

3. The biomimetic reflective material of claim 1, the material having at least a first and a second refractive state, wherein the material in the first refractive state has a refractive index that is different from a refractive index of the material in the second state.

4. A method of producing a biomimetic reflective material comprising providing a first component comprising at least one polypeptide selected from the group consisting of:
   (a) a reflectin polypeptide having at least 87.2% identity to SEQ ID NO:2;
   (b) a polypeptide having at least one and not more than four repeat units of the reflectin polypeptide;
   (c) a polypeptide comprising at least six repeat units of the reflectin polypeptide; and
   (d) any combination of (a) through (c) combining the first component with at least a second component to form a biomimetic reflective material.

5. The method of claim 4, wherein the second component comprises a member of the group consisting of: a metal, an ion, a polymer, a fabric, a crystal, a fiber and a plastic.

6. A method of producing a biomimetic reflective material comprising causing expression in an isolated cell, of at least one polypeptide selected from the group consisting of:
   (a) a reflectin polypeptide having at least 87.2% identity to SEQ ID NO:2;
   (b) a polypeptide having at least one and not more than four repeat units of the reflectin polypeptide;
   (c) a polypeptide comprising at least six repeat units of the reflectin polypeptide; and
   (d) any combination of (a) through (c) using the isolated cell or extract thereof in producing a biomimetic reflective material.

7. The method of claim 6, wherein the isolated cell is selected from the group consisting of: a plant cell, a bacterial cell; a fungal cell, and an animal cell.

8. The biomimetic reflective material of claim 1, wherein the reflectin polypeptide has a predicted isoelectric point above 8.0.

9. The biomimetic reflective material of claim 1, wherein said polypeptide has an activity of a reflectin protein.

* * * * *